(12) United States Patent
Blackhurst et al.

(10) Patent No.: US 10,426,902 B2
(45) Date of Patent: Oct. 1, 2019

(54) SYSTEMS FOR LAPAROSCOPIC SURGERY

(71) Applicant: Fisher & Paykel Healthcare Limited, Auckland (NZ)

(72) Inventors: Michael Joseph Blackhurst, Auckland (NZ); James Alexander Gordon, Auckland (NZ); Jonathan David Harwood, Auckland (NZ); David John Bain, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 97 days.

(21) Appl. No.: 15/333,011

(22) Filed: Oct. 24, 2016

(65) Prior Publication Data

US 2017/0136195 A1    May 18, 2017

Related U.S. Application Data

(63) Continuation of application No. 13/518,295, filed as application No. PCT/NZ2010/000257 on Dec. 20, 2010, now Pat. No. 9,474,512.

(Continued)

(51) Int. Cl.
*A61M 13/00* (2006.01)
*H05B 3/68* (2006.01)
(Continued)

(52) U.S. Cl.
CPC ........... *A61M 13/003* (2013.01); *A61B 17/00* (2013.01); *A61B 18/00* (2013.01); *G01F 22/00* (2013.01);
(Continued)

(58) Field of Classification Search
CPC .. A61M 2205/3368; A61M 2205/3372; A61M 16/16; A61M 16/161;
(Continued)

(56) References Cited

U.S. PATENT DOCUMENTS

| 1,156,145 A | 10/1915 | Jenkins |
| 3,783,262 A | 1/1974 | Pile |

(Continued)

FOREIGN PATENT DOCUMENTS

| DE | 102006018423 | 10/2007 |
| ES | 2208807 | 6/2004 |

(Continued)

OTHER PUBLICATIONS

International Search Report; PCT/NZ2010/00257; dated Mar. 23, 2011; 6 pages.

*Primary Examiner* — Adam Marcetich
(74) *Attorney, Agent, or Firm* — Knobbe Martens Olson & Bear LLP

(57) ABSTRACT

This invention relates to a surgical smoke evacuation system for use in removing gases and smoke created in surgical procedures form within an insufflated surgical cavity. Such a system comprises a discharge assembly adapted to form a gases path, and having an end which in use is located within said surgical cavity so that gases and/or surgical smoke inside said cavity can pass out of said cavity and through said discharge assembly along said gases path, a flexible discharge limb having an operational site end and an outlet end, and a self-supporting wall defining a gases flow passage between said operational site end and said outlet end, in use said open operational site end sealingly connected to said discharge assembly so that said gases and/or surgical smoke can pass out of said discharge assembly and into said discharge limb, a filter connected in use to the outlet end of the discharge limb, at least part of said wall of the discharge limb formed from a breathable material, said breathable material allowing the passage of water vapour through the wall of the discharge limb without allowing the passage of liquid water or surgical smoke or other gases.

26 Claims, 7 Drawing Sheets

Related U.S. Application Data

(60) Provisional application No. 61/289,610, filed on Dec. 23, 2009.

(51) Int. Cl.

| | | |
|---|---|---|
| *G01F 23/22* | (2006.01) | |
| *A61B 18/00* | (2006.01) | |
| *A61B 17/00* | (2006.01) | |
| *G01F 22/00* | (2006.01) | |
| *G08B 21/18* | (2006.01) | |
| *A61M 16/08* | (2006.01) | |

(52) U.S. Cl.
CPC ...... *G08B 21/182* (2013.01); *A61B 2218/006* (2013.01); *A61B 2218/007* (2013.01); *A61B 2218/008* (2013.01); *A61M 16/0808* (2013.01); *A61M 2205/18* (2013.01); *A61M 2205/3327* (2013.01); *A61M 2205/3368* (2013.01); *A61M 2205/3386* (2013.01); *A61M 2205/36* (2013.01); *A61M 2205/75* (2013.01); *A61M 2205/7536* (2013.01); *A61M 2210/1017* (2013.01); *A61M 2210/1021* (2013.01)

(58) Field of Classification Search
CPC .............. A61M 16/162; A61M 16/164; A61M 16/165; A61M 16/167; A61M 16/168; F22B 1/284; F22B 35/18; G01F 23/00; G05D 9/12; A47J 31/56; H05B 2213/04; H05B 2213/07; H05B 3/746; H05B 3/78; H05B 2213/00; H05B 1/0269; H05B 1/0297; H05B 6/804; A62B 9/003
See application file for complete search history.

(56) References Cited

U.S. PATENT DOCUMENTS

| | | | |
|---|---|---|---|
| 3,860,978 A | 1/1975 | Wirth | |
| 3,897,923 A | 8/1975 | Paepke | |
| 4,028,444 A | 6/1977 | Brown et al. | |
| 4,151,864 A | 5/1979 | Thurman | |
| 4,284,878 A | 8/1981 | Bartels | |
| 4,441,027 A | 2/1984 | Richardson et al. | |
| 4,682,010 A | 7/1987 | Drapeau | |
| 4,922,554 A | 5/1990 | Hwang | |
| 5,065,785 A | 11/1991 | Deacon | |
| 5,346,075 A | 9/1994 | Nichols et al. | |
| 5,442,157 A | 8/1995 | Jackson | |
| 5,578,000 A | 11/1996 | Greff | |
| 5,722,393 A | 3/1998 | Bartel et al. | |
| 6,050,530 A | 4/2000 | Nakamura | |
| 6,095,505 A * | 8/2000 | Miller ............... | A61M 16/1075 128/203.27 |
| 6,311,936 B1 | 11/2001 | Herr | |
| 6,469,282 B1 * | 10/2002 | Roberts ................ | H05B 1/0266 219/451.1 |
| 6,523,538 B1 | 2/2003 | Wikefeldt | |
| 7,571,744 B2 | 8/2009 | Zia et al. | |
| 8,640,696 B2 | 2/2014 | Pujol | |
| 9,474,512 B2 | 10/2016 | Blackhurst et al. | |
| 10,220,177 B2 | 3/2019 | McAuley et al. | |
| 2002/0129815 A1 | 9/2002 | McPhee | |
| 2003/0154977 A1* | 8/2003 | White ............... | A61M 16/1075 128/203.26 |
| 2003/0183082 A1 | 10/2003 | Schultz | |
| 2004/0016430 A1* | 1/2004 | Makinson ............ | A61M 16/10 128/203.12 |
| 2004/0020487 A1 | 2/2004 | Koch et al. | |
| 2004/0055597 A1 | 3/2004 | Virr et al. | |
| 2004/0079370 A1 | 4/2004 | Gradon et al. | |
| 2004/0102731 A1* | 5/2004 | Blackhurst ......... | A61B 1/00154 604/26 |
| 2004/0221844 A1 | 11/2004 | Hunt et al. | |
| 2005/0054993 A1 | 3/2005 | Falahee | |
| 2005/0241714 A1 | 11/2005 | Barnhouse | |
| 2006/0113690 A1* | 6/2006 | Huddart ............ | A61M 16/1075 261/129 |
| 2006/0162726 A1 | 7/2006 | Smith | |
| 2007/0000908 A1* | 1/2007 | Bohan, Jr. ................ | F24F 11/30 219/505 |
| 2007/0137484 A1 | 6/2007 | Roberts | |
| 2007/0193871 A1* | 8/2007 | Wiseman ............. | B01D 1/0082 202/185.3 |
| 2007/0225664 A1 | 9/2007 | Schultz et al. | |
| 2007/0272239 A1 | 11/2007 | Aylsworth et al. | |
| 2007/0284361 A1 | 12/2007 | Nadjafizadeh et al. | |
| 2007/0289449 A1 | 12/2007 | Roberts | |
| 2009/0078260 A1 | 3/2009 | Smith et al. | |
| 2009/0107493 A1* | 4/2009 | Liu ................... | A61M 16/1075 128/202.22 |
| 2009/0110379 A1* | 4/2009 | McGhin ............ | A61M 16/1075 392/485 |
| 2009/0134282 A1 | 5/2009 | Grim | |
| 2009/0184832 A1* | 7/2009 | Lloyd ................ | A61M 13/003 340/635 |
| 2009/0223514 A1 | 9/2009 | Smith et al. | |
| 2009/0229606 A1* | 9/2009 | Tang ................. | A61M 16/0051 128/203.14 |
| 2010/0248176 A1* | 9/2010 | Anderson ............. | F24H 9/2035 432/4 |
| 2011/0083562 A1* | 4/2011 | Ryan .................... | H05B 1/0261 99/323.7 |
| 2011/0147376 A1* | 6/2011 | Ueda ..................... | F24C 15/327 219/682 |
| 2011/0162647 A1 | 7/2011 | Huby et al. | |
| 2017/0136195 A1 | 5/2017 | Blackhurst et al. | |

FOREIGN PATENT DOCUMENTS

| | | |
|---|---|---|
| GB | 2224957 A | 5/1990 |
| GB | 2460645 A | 12/2009 |
| WO | WO 99/59661 | 11/1999 |
| WO | WO 2006/015416 | 2/2006 |
| WO | WO 2011/078706 | 6/2011 |

\* cited by examiner

SYSTEMS FOR LAPAROSCOPIC SURGERY

CROSS-REFERENCE TO RELATED APPLICATIONS

This application is a continuation of U.S. patent application Ser. No. 13/518,295, filed Jan. 2, 2013, which is hereby incorporated by reference herein. U.S. patent application Ser. No. 13/518,295 is National Phase Application of PCT International Application Number PCT/NZ2010/000257, filed Dec. 20, 2010 which claims priority benefit of U.S. Provisional Application No. 61/289,610 filed on Dec. 23, 2009, each of which is hereby incorporated by reference in their entirety.

FIELD OF THE INVENTION

The present invention relates to insufflation systems and smoke evacuation systems for laparoscopic procedures or electrosurgery or electrocautery procedures.

BACKGROUND TO THE INVENTION

Laparoscopic surgery, also called minimally invasive surgery (MIS), or keyhole surgery, is a modern surgical technique in which operations in the abdomen are performed through small incisions (usually 0.5-1.5 cm) as compared to larger incisions needed in traditional surgical procedures. Laparoscopic surgery includes operations within the abdominal or Pelvic cavities.

In abdominal surgery, for example, the abdomen is usually insufflated with carbon dioxide gas to create a working and viewing space. The abdomen is blown up like a balloon (insufflated); elevating the abdominal wall above the internal organs like a dome. The gas used is generally $CO_2$, which is common to the human body and can be absorbed by tissue and removed by the respiratory system. It is also non-flammable, which is important because electrosurgical devices are commonly used in laparoscopic procedures. FIG. 1 shows a diagram of a typical laparoscopic procedure, with part of the outer layers of the body not shown so as to show interior detail.

The purpose of insufflation is to create a working space within the body for carrying out surgical procedures which frequently can involve electrosurgery or electrocautery. Lasers are also becoming increasingly popular in modern surgical procedures. The use of these devices tends to create surgical smoke in the working space due to burning of tissue. Smoke evacuation systems which use a discharge limb are commonly used to remove the smoke from the surgical site, so that a surgeon can see what he or she is doing, and so that this potentially harmful material does not remain within the body cavity post-surgery. One end of the discharge limb is connected to, or inserted into, a second incision (or sometimes the same incision). A typical smoke evacuation system generally includes a trocar and a cannula at the end to aid insertion into the operative site. The smoke exits the insufflated abdominal area through the discharge limb. The discharge limb may be attached to the end of a laparoscopic instrument so as to provide evacuation close to the site where electrocautery takes place. Usually, the gases and smoke from the body cavity are filtered through a filter to remove particulate matter before they are vented to atmosphere. The filter may also be additionally designed to remove chemicals and any harmful micro-organisms from the surgical smoke. U.S. Pat. Nos. 5,578,000, 6,110,259 and 5,226,939 all describe examples of surgical smoke evacuation systems. Commonly available surgical smoke evacuation systems include, for example, the SmartVac® smoke evacuation system and the SeeClear® MAX smoke evacuation system. The smoke filter is usually located at the other end of the discharge limb from that end which is inserted into the incision.

Commonly, a vacuum source is connected to the other end of the discharge limb—the end furthest from the patient. The vacuum source may be a wall vacuum or a standalone vacuum device. The vacuum creates a negative pressure within the operative site to 'suck out' smoke and any excess insufflation gases. In an arrangement where a vacuum source is used, it is usual to position the filter at a point along the conduit generally just upstream, of the vacuum source to remove the undesirable contaminants from the evacuated smoke.

Current smoke evacuation systems use plastic tubing (generally PVC tubing), for the discharge limb. The atmosphere within a patient's abdominal cavity is generally humid, and the heat of surgical operations such as electrocautery tends to add to the humidity as the heat causes moisture to evaporate from the patient's internal organs. It has been common practice in laparoscopic surgery to use dry gases. However, it is also desirable for the $CO_2$ or other insufflation gas to be humidified in a similar fashion to how gases are humidified for respiratory therapy e.g. CPAP or similar. In insufflation applications, the gases are humidified before they are passed into the abdominal cavity. This can help prevent 'drying out' of the patient's internal organs, and can decrease the amount of time needed for recovery from surgery.

Smoke evacuation systems are commonly used with insufflation systems. Insufflation systems deliver humidified gases into an incision to create a working space within the body for electrocautery surgery, electro-surgery or laparoscopic procedures. Insufflation systems generally comprise humidifier chambers that hold a quantity of water within them. The humidifier generally includes a heater plate that heats the water to create a water vapour that is transmitted into the incoming gases to humidify the gases. The gases are transported out of the humidifier with the water vapour. The humidification chamber requires a minimum level of water to allow the humidification chamber to adequately humidify incoming gases. Accordingly a health professional or person using the insufflation system needs to keep checking the water level in the humidification chamber and add more water when required. This job can be tedious one and is often overlooked. U.S. Pat. No. 6,802,314 discloses a method of monitoring the level of water in a humidification chamber. The method is implemented on an electronic controller that controls the humidifier heater plate operation and operation of the blower used with the humidifier. The method involves monitoring the temperature of the heater base 102, the temperature of the humidification chamber 103 (or chamber outlet temperature) and the power requirement of the heater base (the amount of power being supplied to the heater base). Thermal conductivity is calculated using the measured values. Thermal conductivity is calculated by the heater base power requirement divided by the heater plate temperature minus the chamber temperature.

The controller compares the calculated thermal conductivity value to a predetermined threshold value which may be experimentally determined at various gases flow rates. The predetermined threshold values can be stored in ROM and be accessible to the controller so that the controller would simply determine the present flow rate of the gases, calculate the value of thermal conductivity, access the table in ROM based on the present flow rate and read out the associated predetermined threshold value. If the calculated thermal conductivity is greater than the thermal conductivity value then the controller would wait a predetermined time before issuing an alarm so that the water level could be topped up without any loss of humidity in the gases flow.

It is an object of the present invention to at least partially help to overcome these problems and other defects in the prior art, or at least provide the public with a useful alternative.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

In a first aspect the invention may broadly be said to consist of a surgical smoke evacuation system for use in removing gases and smoke created in surgical procedures from within an insufflated surgical cavity, said cavity of the type that has at least one aperture adapted for gases discharge, said surgical smoke evacuation system comprising
  a discharge assembly adapted to form a gases path, and having an end which in use is located within said surgical cavity so that gases and/or surgical smoke inside said cavity can pass out of said cavity and through said discharge assembly along said gases path,
  a flexible discharge limb having an operational site end and an outlet end, and a self-supporting wall defining a gases flow passage between said operational site end and said outlet end, in use said open operational site end sealingly connected to said discharge assembly so that said gases and/or surgical smoke can pass out of said discharge assembly and into said discharge limb,
  a filter connected in use to the outlet end of the discharge limb,
  at least part of said wall of the discharge limb formed from a breathable material, said breathable material allowing the passage of water vapour through the wall of the discharge limb without allowing the passage of liquid water or surgical smoke or other gases.

Preferably said breathable material comprises at least 10% of said wall of said discharge limb surface area.

Preferably said wall has an internal diameter of between 10 mm and 25 mm.

Preferably said discharge limb is between 400 mm and 1500 mm long.

More preferably said discharge limb is 470 mm long.

Preferably said smoke evacuation system is a passive-smoke evacuation system, said surgical cavity pressurised due to insufflation gas being pumped into said surgical cavity from a pressurised gases source so, that said conduit has a higher pressure at the operative site end than at said outlet end, said downstream exit aperture open to atmosphere.

Preferably said breathable material is a hydrophilic thermoplastic.

Alternatively said breathable material is a perfluorinated polymer.

As a further alternative said breathable material is made from woven treated fabrics.

Preferably said smoke evacuation system further comprises a support to receive and retain said discharge limb in a manner such that said limb is bent along its length where said limb attaches to said support, said bend in said limb shaped, such that in use said filter is not the lowest point of the limb, said lowest part of the bend being the lowest part of the limb.

Preferably said support has at least one and preferably two receiving features to receive and retain said discharge limb, said receiving feature or features arranged in a manner relative to each other, to create a U bend within said limb when limb is housed within said feature or features.

Preferably said U bend behaves substantially like a water trap such that any condensation of liquid within said discharge limb flows toward U bend and accumulates close to the lowest point of said U bend.

Preferably said receiving features are slots or rings and said limb snap fits into said slots or rings.

Preferably said support is substantially U shaped.

Preferably said receiving features are positioned at or close to opposing ends of said support.

Preferably in use said support maintains at least two contact points with the ground to form a stable structure to retain and hold up said limb.

In a further aspect of the support said support further comprises at least two legs extending from said support, said legs contacting the ground and propping up said support in an upright position.

Preferably said legs of said support provides two of three said contact points with the ground, at least part of the body of said support providing the third of said three contact points with the ground.

Preferably said support includes a further stand member, said stand member and said legs forming three contact points with the ground.

Preferably wherein said support includes at least one righting mass within the support or attached to the support, said righting mass stabilising the support such that said support and limb remain in correct orientation in use.

Preferably said righting mass is a movable mass.

Alternatively said righting mass is a stationary mass.

Preferably said righting mass in Made from a rigid material, said material being denser than said support.

Preferably said support is formed from a rigid material.

More preferably wherein said support is formed from moulded plastic.

In a further alternate aspect said system includes a retaining member engaging with said smoke evacuation limb, said retaining member adapted to bend or contort said limb such that in use said filter is not the lowest point of the limb.

Preferably said retaining member is attached to said filter at one end of said retaining member, an opposing end of said retaining member including a retaining feature adapted to receive and retain said limb up stream of said filter such that said limb is bent or contorted such that said filter is not the lowest point of said limb.

Preferably said limb is bent or contorted to form a U bend in use, said U bend acting as a water trap such that any condensation or liquid within said limb flows toward said Ti bend and accumulates near the lowest point of said U bend.

Preferably said retaining feature is a hook or loop, said hook or loop adapted to receive and retain said limb such that said limb upstream of said filter is bent or contorted.

Alternatively wherein said retaining feature is a clip, said clip adapted to receive and retain said limb such that said limb upstream of said filter is bent or contorted.

In a further preferable aspect said breathable material forms a flow path for water vapour from the inside of said discharge limb to ambient air, such that said water vapour can pass from inside the discharge limb to ambient air through the breathable material forming at least part of said wall of said discharge limb.

Alternatively said water vapour is absorbed by the breathable-material on the inside of said discharge limb said absorbed water passing through said wall of said discharge limb to atmosphere, said breathable material preventing water condensate and particulate matter passing through said wall.

Preferably said wall of said discharge limb comprises multiple regions of said breathable material.

Alternatively said regions of breathable material are elongate and run at least a substantial length of said discharge limb.

Preferably said breathable material regions are spaced along the length of said discharge limb.

Preferably said regions of breathable material are formed as elongate strips along the wall of said discharge limb.

In a second aspect the invention can be said to broadly consist of a surgical smoke evacuation system for use in removing gases and smoke created in surgical procedures from within an, insufflated cavity, said cavity of the type that has at least one aperture adapted for gases discharge, said surgical smoke evacuation system comprising:
- a discharge assembly adapted to form a gases path, and having an end which in use is located within the surgical cavity so that gases and/or surgical smoke inside the cavity can pass out of the cavity and through said discharge assembly along said gases path,
- a flexible discharge limb having an operational site end and an outlet end, and a self-supporting wall defining a gases flow passage between the operational site end and the outlet end, in use the operational site end sealingly connected to, the discharge assembly so that the gases and/or surgical smoke can pass out of the discharge assembly and into the discharge
- a filter muse connected to the outlet end of the discharge limb,
- a support adapted to receive and retain said discharge limb in a manner such that said limb is bent along part of the discharge limb's length where the support contacts the limbs, such that in use the bend along part of said discharge limb's length acts to collect any condensation formed within the discharge limb, said limb being bent such that in use said filter in not the lowest point of said limb.

Preferably said bend in said discharge limb in substantially a U shaped bend, said U shaped bend acting as a condensation collection point to collect any condensation formed in said discharge limb, said U bend also preventing said condensation, from flowing along the limb to the filter or the outlet of the limb.

Preferably said support has two receiving features to receive and retain said limb.

Preferably-said receiving features are slots or rings adapted such that said limb snap fits into said slots or rings.

Preferably said support is substantially U shaped and includes a channel to receive and retain said limb within said support.

Preferably said receiving features are positioned at opposing ends of said support.

Preferably said support includes a righting mass attached to or housed within said support, said righting mass stabilising said support such that said support remains in the correct orientation when in use.

In an alternate form of the support said support is a retaining member extending from said filter, said retaining member engaging with said limb, said limb being bent or contorted by said retaining member, such that said filter is not the lowest point of said limb.

Preferably said retaining member including a retaining feature that receives and retains said limb, said retaining feature bending said limb such that said filter is not the lowest point of said limb.

Preferably wherein said retaining feature is hook or loop.

In a further aspect of the support said support comprises a body having a first end and a second end, said first end is connected to said outlet end of said discharge, limb, said second end of said support connected to said filter, said support forming a scaled gases pathway to allow flow of gases and/or smoke from the outlet end of the discharge limb to the filter, the gases and/or smoke travelling through said support.

Alternatively said support comprises a body having a first end and a second end, said first end connecting to the outlet end of said discharge limb, said second of said support connecting to a substantially flexible secondary conduit, said filter connected to said secondary conduit, said support forming a sealed gases pathway to allow the flow gases and/or smoke from the outlet end of said discharge limb to secondary conduit, said gases and/or smoke travelling through said support.

Preferably said first and second end of said support comprise threaded connections to connect first end to said discharge limb and connect second end of support to either said filter or said secondary conduit.

Alternatively said first and second end of said support include couplers.

Preferably said support maintains at least two contact points with the ground to form a stable structure retain and hold up said smoke evacuation limb.

Preferably said support includes at least two legs extending from said support, said legs in use contacting the ground and propping up said support in an upright position.

Preferably said legs of said support provides two of three said contact points with the ground and the body of said support provides the third, of said three contact points with the ground.

Preferably said support is formed from a rigid material.

Preferably said support is formed from moulded plastic.

In a further alternative aspect at least part of said support is formed from a breathable material, said breathable material allowing the passage of water vapour through said support to ambient air without allowing the passage of said liquid water or surgical smoke.

As a further alternative the entire support is formed from a breathable material.

In a further aspect at least part of said secondary conduit is formed from a breathable material such that said breathable material allows the passage of water vapour out of said secondary conduit to ambient air without allowing the passage of liquid water or surgical smoke or gases.

Preferably at least part of wall of said discharge limb is formed from a breathable material, said breathable material allowing the passage of water vapour through the wall of the discharge limb without allowing the passage of liquid water or surgical smoke or other gases.

More preferably said breathable material comprises at least 10% of said wall of said discharge limb surface area.

Preferably said wall has an internal-diameter of between 10 mm and 25 mm.

Preferably said discharge limb is between 400 mm and 1500 mm long:

More preferably said discharge limb is 470 mm long.

Preferably said smoke evacuation system is a passive smoke evacuation system, said surgical cavity pressurised due to insufflation as being pumped into said surgical cavity from a pressurised gases source so that said conduit has a higher pressure at the operative site end than at said outlet end, said downstream exit aperture open to atmosphere.

In one form said breathable material is a hydrophilic thermoplastic.

In an alternate form said breathable material is a perfluorinated polymer.

In a further alternate form said breathable material is made from woven treated fabrics.

Preferably the surface area of said discharge limb is between 12560 mm$^2$ and 47100 mm$^2$.

Preferably said system further comprises a further conduit arranged co-axially with said discharge limb, said further conduit arranged around the outside of said discharge limb to cover said discharge limb, said further conduit acting as an air jacket, in use said water vapour passing through the breathable material of said discharge limb into the air in said conduit, said conduit transporting water vapour away from said breathable areas of said discharge limb.

In a third aspect the invention can be broadly said to consist in an insufflation system comprising:
  a gases source,
  a humidification chamber adapted to hold a volume of water having and inlet and an outlet, said inlet of said humidification chamber in gases communication with said gases source to receive gases from said gases source, said gases coming in through said inlet and passing through said outlet of said humidification chamber,
  a conduit having a first end and a second end, said first end connected to said outlet of said humidification chamber, said first end of said conduit in gases communication with said humidification chamber outlet and receiving said humidified gases from said humidifier, said second of said conduit in communication with a surgical site and delivering said humidified gases to said surgical site,
  a heater base provided adjacent said humidification chamber, said heater base providing heat to said quantity of water in said humidification chamber in order to provide water vapour to said gases flowing through said humidification chamber,
  a first temperature sensor attached to said heater base and monitoring temperature of said heater base,
  a second temperature sensor attached adjacent to said outlet of said humidification chamber, said second temperature sensor monitoring said temperature of said humidification chamber,
  a controller adapted to control heat provided by said heater base to said humidification chamber, said controller connected to said first and second temperature sensors and receiving temperature information from said sensors.

Preferably said controller implements a method to determine a low water or no water condition in said humidification chamber, said method comprising the steps of:
  measuring the temperature of gases exiting the chamber,
  measuring the power supplied to a heater base,
  measuring the flow rate of gases through the chamber,
  determining a low water or no water condition when the temperature of the gases exiting the chamber is decreasing, the power supplied to the heater base is constant or increasing and the flow rate of gases through the chamber is unchanged, for at least two minutes.

In one form said system includes a buzzer, said buzzer operation controlled by said controller when said low water or no water condition is detected.

Preferably said controller switches off power to said heater base when a low water or no water condition is detected.

In a fourth aspect the invention can be broadly said to consist in a method to determine a low water or no water condition in a humidification chamber, said humidification chamber part of an insufflation apparatus for providing humidified insufflation gases in to a surgical site or peritoneal cavity of a patient to insufflate said cavity or said surgical site, said method comprising the steps of:
  measuring power supplied to a heater base,
  measuring the temperature of gases exiting said humidification chamber,
  measuring flow rate of gases through said humidification chamber,
  determining a low water or no water condition based on a reducing temperature of gases exiting said humidification chamber, while said power to said heater is constant or increasing and the flow of gases through said chamber is constant for a pre-determined time.

Preferably said method includes the step of:
  said pre-determined time is at least two minutes, said controller switching off power to said heater base if a low water or no water condition is measured.

Preferably said method comprises the further step of alerting a user when a low water or no water condition is detected.

Preferably said low water or no water condition is determined if said temperature of gases exiting said chamber reduces while said power to said heater base increases for at least two minutes.

Preferably said filter includes an adjustable outlet port connected to said filter, said outlet port allowing a user to adjust the amount of gases flowing out of said filter.

In a fifth aspect the invention can be broadly said to consist in a discharge limb for use in a surgical smoke evacuation system for evacuating surgical smoke and gases from a surgical site in or on a patient said discharge limb comprising:
  a flexible elongate hollow body defining a gases transportation pathway for transporting smoke and gases created in surgical procedures,
  said body having a operative site end adapted for connection to the surgical site, an outlet end adapted to connect to a filter, said surgical smoke and gases substantially travelling from said surgical the to said filter through said elongate hollow body,
  the elongate hollow body being at least partially constructed from a breathable material or region allowing the passage of water vapour out of the elongate hollow body through the breathable region or material while restricting the passage of liquid water or surgical smoke and gases.

Preferably said water vapour is passed from the elongate body to ambient air through the breathable region or material.

Preferably said limb further includes an air jacket arranged coaxially with said elongate hollow body, said air jacket covering and enclosing said elongate hollow body, said water vapour passing through the breathable region or material into said air jacket.

Preferably said air jacket is formed by a further conduit arranged co-axially with said elongate hollow body.

Preferably said breathable material comprises at least 10% of the surface area of said discharge limb.

Preferably said discharge limb has an internal diameter between 10 mm and 25 mm.

Preferably said discharge limb is between 400 and 1500 mm long.

More preferably said discharge limb is 470 mm long.

Preferably said discharge limb has a higher pressure at the operative site end adapted to connect to a surgical site and a lower pressure at the outlet end adapted to connect to the filter, said pressure differential causing said surgical smoke and gases to move from said surgical site to said filter through said elongate hollow body.

In one form said breathable material is a hydrophilic thermoplastic.

Alternatively said breathable material is a perfluorinated polymer.

Alternatively said breathable material is made from woven treated fabrics.

Preferably the limb further comprises:
 a support, said limb attaching to said support, said support adapted to hold up said discharge limb in use in a manner such that said limb is bent along its length where said limb. attaches to said support, said bent in said limb shaped such that said filter is not the lowest point of the limb, said lowest part of the bend being the lowest part of the limb.

Preferably said support includes at least but more preferably two receiving features to receive and retain said discharge limb, said receiving said features arranged in a manner relative to each other to create a U bend within said limb when limb placed within said feature or features.

Preferably said U bend behaves substantially like a water trap such that any condensation of liquid within said smoke evacuation limb flows toward U bend and accumulates close to the lowest point of said U bend.

Preferably said support maintains at least two contact points with the ground to form a stable structure to retain and hold up said limb.

Preferably said support includes at least two legs extending from said support, in use said legs contacting the ground and propping up said support in an upright position.

More preferably in use said legs of said support provide two of three said contact points with the ground and body of said support providing the third of said three contact points with the ground.

Preferably said support includes a further stand member, said stand member and said legs in use forming three contact points with the ground.

Preferably said support includes at least one righting mass within the support or attached to the support, said righting mass stabilising the support such that said support and limb remain in correct orientation.

Preferably said righting mass is a movable mass.

Alternatively said righting mass is a stationary mass.

Preferably said righting mass is made from a rigid material, said material being denser than said support.

Preferably said support is formed from a rigid material.

More preferably said support is formed from moulded plastic.

In a further aspect said support is a retaining member extending from said filter, said retaining member engaging with said limb, said limb being bent or contorted by said retaining member, such that in use said filter is not the lowest point of said limb.

Preferably said retaining member includes a retaining feature that receives and retains said limb, said retaining feature bending said limb such that said filter is not the lowest point of said limb in use.

Preferably said retaining feature is a hook or loop.

Preferably said limb is adapted to connect to a surgical site through a discharge assembly adapted to form a gases path, said discharge assembly having one end which in Use is located within said surgical site so that gases and/or surgical smoke inside the cavity can pass out of said cavity through said discharge assembly along the gases path into the discharge limb.

Preferably said discharge limb includes a first connector on said operative site end of said limb and a second connector on said outlet end of said limb.

Preferably said first connector is a luer lock connector, said first connector adapted to connect to said discharge limb, said second connector being a barbed connector adapted to connect to said filter.

In a sixth aspect the invention can be said to broadly consist in a kit of parts for an unassembled surgical smoke evacuation system for use on removing gases and smoke created in surgical procedures from with an insufflated cavity, said kit for an unassembled surgical smoke evacuation system comprising:
 a flexible discharge limb having an operative site end and an outlet end, said limb being an elongate hollow body, said hollow body defining a gases transport path, said hollow body or at least part of said hollow body formed from a breathable material, said breathable material allowing the passage of water vapour but not liquid water through said hollow body,
 a filter with two ends, one end of the filter connectable to the outlet end of said discharge limb,
 a discharge assembly having one end which can be located within a surgical cavity and another end connectable to said operative site end of said limb, said discharge assembly adapted to form a gases path between the two ends of said discharge limb,
 said flexible discharge limb, said filter and said discharge assembly connecting together to form said surgical smoke evacuation system.

Preferably said kit further comprising:
 a support, said support including at least one receiving feature, and at least two legs extending from said support, said receiving feature capable of receiving and retaining said limb within it such when said kit is assembled and said limb is engaged within said receiving feature said limb is bent such that said filter is not the lowest point.

Preferably said kit further comprising.
 a retaining member attached to said filter, said retaining member being an elongate member, said retaining member including a retaining feature at one end of said retaining member, said retaining feature connectable with said limb in use such that in use said limb is bent such that said filter is not the lowest point.

The term smoke evacuation limb and discharge limb are interchangeably used and refer to the same physical feature.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

As used herein the term "and/or" means "and" at "or", or both. As used herein "(s)" following a noun means the plural and/or singular forms of the noun.

DETAILED DESCRIPTION

System Overview

The preferred embodiments of the present invention will now be described in detail with reference to the figures.

Figure 2:
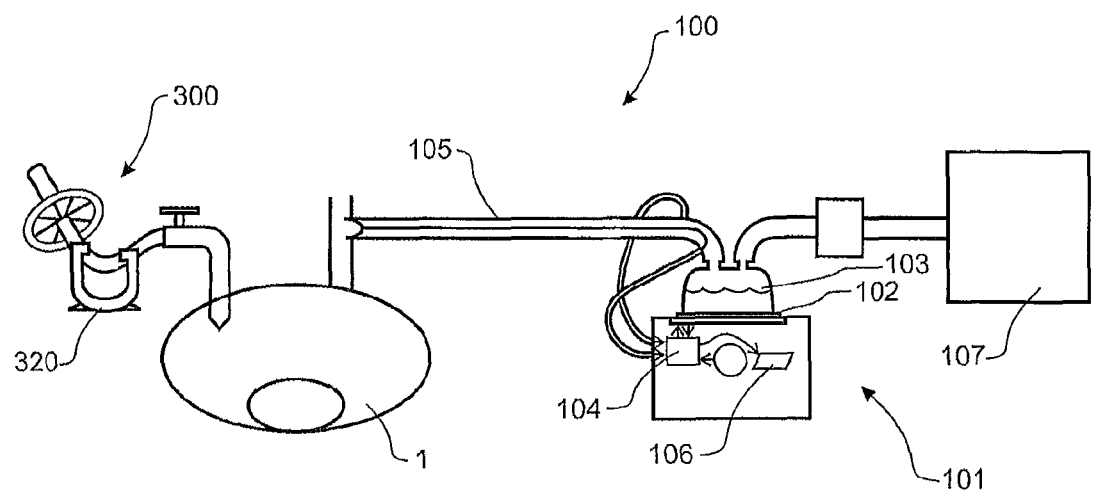
FIG. 2 shows a laparoscopic humidification system in use with a patient receiving humidified gases from the system, and a discharge limb according to the present invention carrying these gases away from the surgical site.
Figure 7:
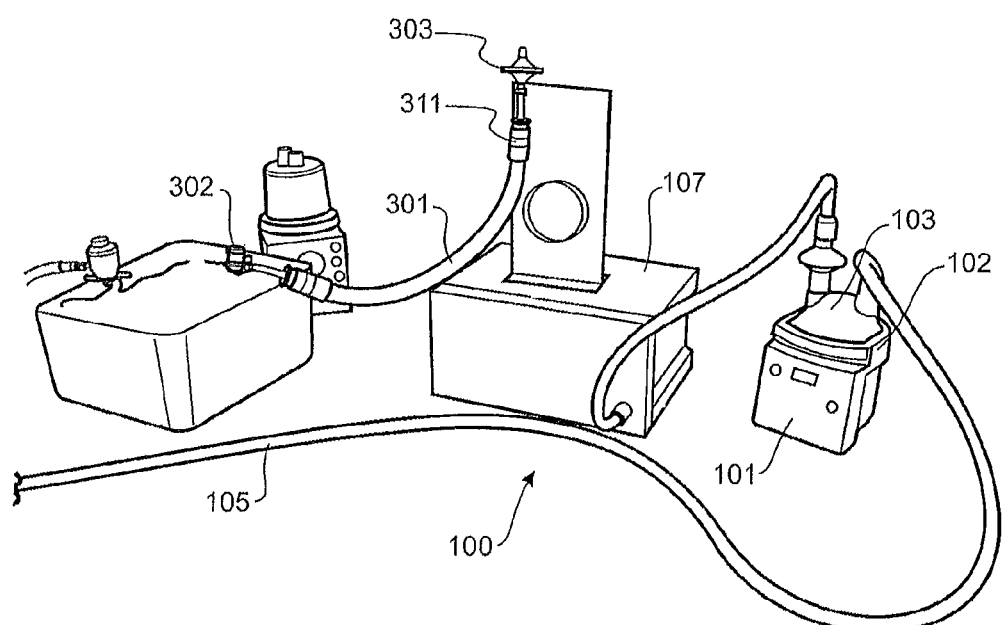
FIG. 7 shows test setup used in testing the effectiveness of a breathable discharge limb used with the smoke evacuation system. The figure shows an insufflation system and the smoke evacuation system used with the patient model of FIG. 4.

FIG. 2 and FIG. 7 shows a typical insufflation system 100 such as might be used with the present invention. The insufflator system supplies insufflation gases to a patient 1. The insufflation system 100 includes an insufflator 101 that humidifies a stream of gases supplied by a gases source 107. The humidified insufflation gases are delivered, at a pressure above atmospheric pressure, into the patient's abdominal or peritoneal cavity. The insufflator 101 includes a heater base 102 and humidifier chamber 103, with the chamber 103 in use in contact with the heater base 402 so that the heater base provides heat to the chamber. The insufflation gases are passed through the chamber 103 so that they become humidified to an appropriate level of moisture. The system includes a delivery conduit 105 that connects between the humidification chamber 103 and the peritoneal cavity or surgical site. The conduit has a first end and second end, the first end being connected to the outlet of the humidification chamber 103 and receiving humidified gases from the chamber 103. The second end of the conduit is placed in the surgical site or peritoneal cavity and humidified insufflation gases travel from the chamber 103, through the conduit and into the surgical site to insufflate and expand the surgical site or peritoneal cavity. The system also includes a controller 104 that regulates the amount of humidity supplied to the gases by controlling the power supplied to the heater base 102. The controller can also be used to monitor water in the humidification chamber and determine a low water or no water condition, which will be described later. A smoke evacuation system 300 is shown leading out of the body cavity of the patient. This will be described in detail below.

Typically, the insufflator pressure will be set between 9 mm/Hg and 15 mm/Hg depending on the size of the patient and the amount of inflation required. The flow rate of the insufflator is set to between 1 L/min and 5 L/min depending on the requirements of the specific operation. In the most preferred form carbon dioxide is used as the insufflation gas.

Figure 3:
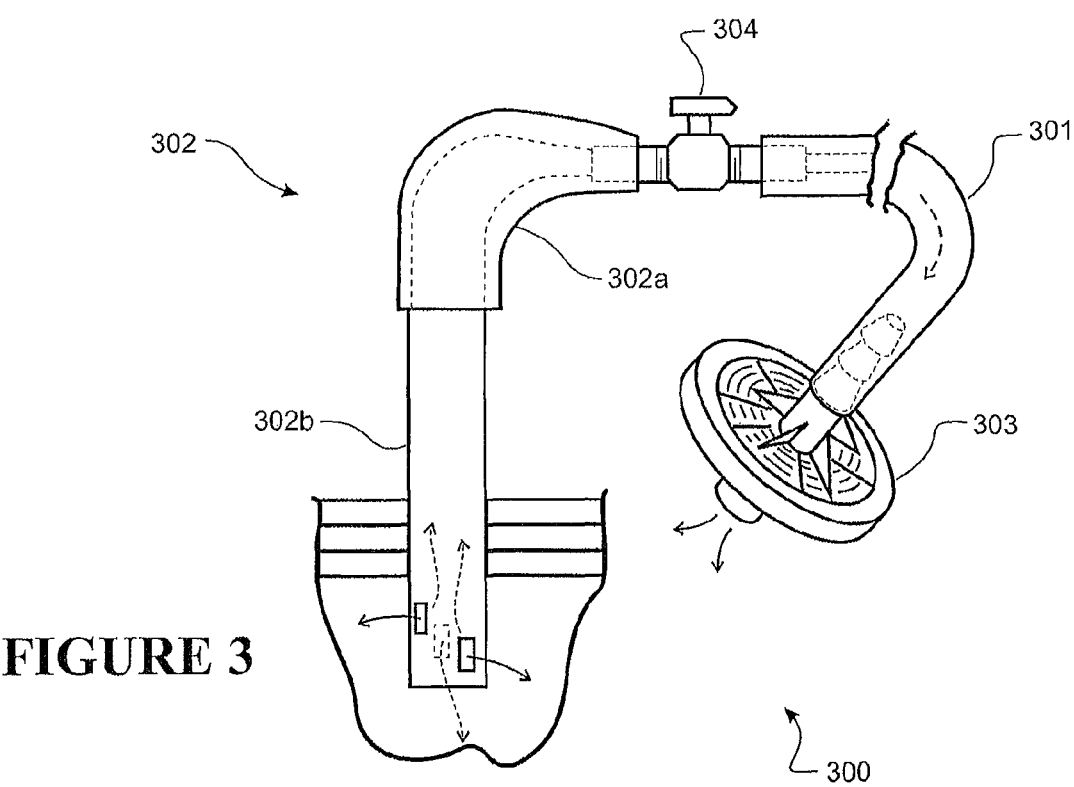
FIG. 3 shows a detailed view of the smoke evacuation system of FIG. 2.
Figure 6:
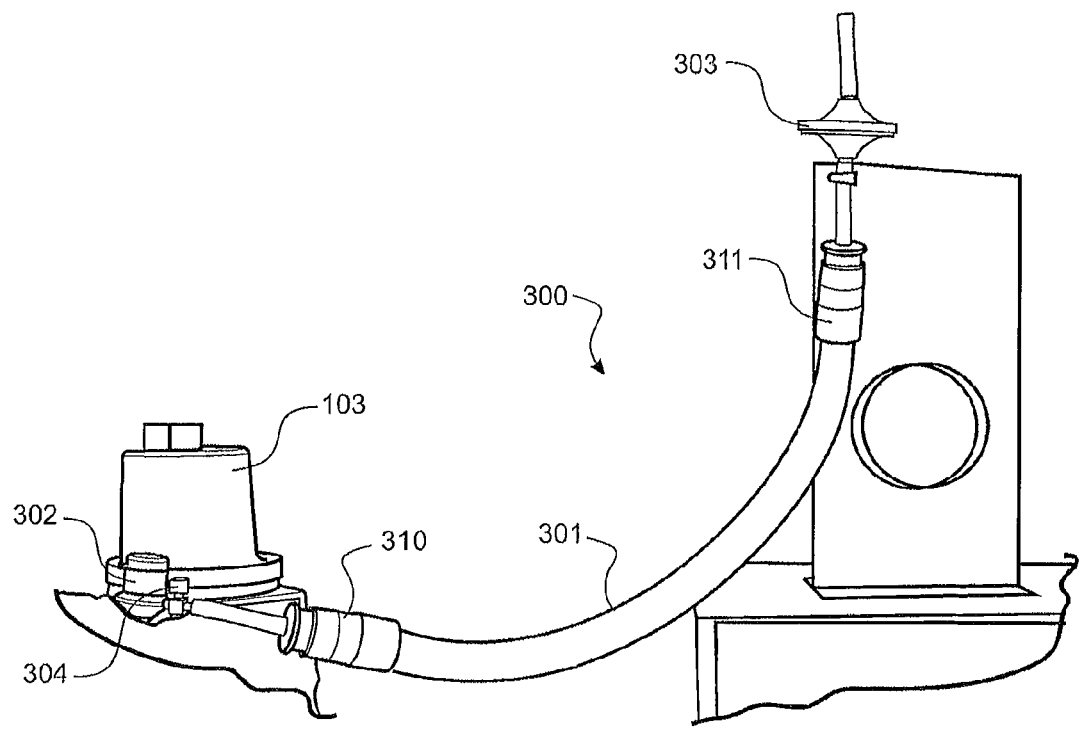
FIG. 6 shows an operative position of the smoke evacuation system when in use with the patient model shown in FIG. 4.

FIG. 3 and FIG. 6 show a more detailed view of the smoke evacuation system 300 of the present invention. The smoke evacuation system can be used in conjunction with the insufflation system 100 described above or may be used with other suitable insufflation systems. The smoke evacuation system 300 comprises a discharge limb 301, a discharge assembly 302 and a filter 303. The discharge limb 301 connects between the filter 303 and the discharge assembly 302, which in use is located in or adjacent to the operative site (peritoneal cavity, for example as indicated by item C in FIG. 1). Preferably the discharge limb 301 is a self-supporting conduit or tube (the conduit is capable of supporting its own weight without collapsing) with two open ends: an operative site end and an outlet end. The discharge limb, in FIG. 3 is shown with a broken line to show that it is long and the length could be variable. The term discharge limb and smoke evacuation limb is interchangeably used in this specification, both terms refer to the same feature. Preferably the discharge limb includes a first connector 310 on the operative site end and a second connector 311 on the outlet end.

In the preferred embodiment, the operative site end includes or is adapted for connection to the discharge assembly 302, which comprises a luer taper 302a and a cannula port 302b. The first connector 310 allows connection of the operative site end to the discharge assembly 302. The first connector is any suitable connector, most preferably a luer lock connector. The luer taper 302a allows the operative site end to be connected to the cannula port 302b. In use, one open end or part of the cannula port 302b is placed or located into the surgical cavity, such as that indicated by item C iii FIG. 1 (i.e. the operative site), via a small incision or similar.

Preferably the cannula port 302b is 5.5 mm in diameter. It is most preferred that the cannula port 302b includes a stopcock 304 that can be opened or closed to act like an on/off valve. Any other moveable obstruction can lie used as an alternate to the stopcock 304. With the cannula port open, the discharge limb 301 is open to the surgical cavity and surgical smoke created within the surgical cavity can flow into the discharge limb 301. With the cannula port in the closed position the discharge limb 301 is sealed off from the surgical cavity and no smoke or gas flows into the discharge limb 301.

The discharge limb 301 has a filter unit 303 connected to the outlet end. The second connector 311 allows the outlet end of the discharge limb to connect to the filter by a suitable connection. The second connector is any suitable connector, most preferably a barbed connector. The filter unit 303 comprises a hard shell, which surrounds a filter medium and holds the filter medium in position. The filter unit has two ends or sides: an upstream end or side, connected to the outlet end of the discharge limb 301, and a downstream end or side that either opens to atmosphere, or which is adapted to in use be connected to a vacuum source. In the preferred embodiment, the downstream side or end of the filter opens to atmosphere. The body of the filter unit 303 also defines a gases flow path between the upstream side and downstream side so that the surgical smoke and other gases in use pass through the filter unit 303, and through the filter medium within the filter unit. The filter medium comprises a filter material or filter media that is adapted to filter gases passing through the filter and leave a (cleaned) residual gas. Preferred filter media includes carbon or is made of UPLA (ultra low particulate air) grade hydrophobic glass microfiber.

The filter media is adapted to filter or trap as much of the contaminant material in the gas as possible. That is, particulate material, odours and gaseous hydrocarbons are, as far as possible, removed from the surgical smoke. The filter passes the residual gas remaining after the filter process. In the preferred embodiment, the gas is passed to atmosphere. The residual gas is almost 100% carbon dioxide. Preferably the filter removes 99.999% of all particles, cells and viruses and has retention up to 0.02 microns.

In the preferred embodiment described above, the smoke evacuation system 300 is a passive smoke evacuation system, meaning that it does not require a vacuum source or any other equivalent device to draw the surgical smoke through the discharge limb 301 of the system. The mechanism for evacuating smoke through the discharge limb 301 will now be explained: the insufflation system is activated and the surgical site is pumped with carbon dioxide gas. The surgeon begins the surgical procedures once the surgical site is inflated to the correct level. Once the flow rates and temperatures of the insufflation system have stabilised the smoke evacuation system can be activated (by opening the stopcock 304). The insufflation system delivers the insufflation gases at a positive pressure.

The stopcock 304 as described above is opened to allow the gas to travel through the cannula port 302b and through the discharge limb 301. The smoke travels through the discharge limb 301, through the filter unit 303 and out through the outlet end. The smoke is "purified" by the filter 303. The filter 303 retains particulate matter, viruses, odours, noxious fumes and other potentially harmful particles. In an alternate form the filter may further include an adjustable outlet port on said filter. The port is an outlet port that allows the user to vary the flow of gases out of said filter. The adjustable outlet port also can function as an on/off switch for the smoke evacuation system. Since the smoke evacuation system is preferably a passive smoke evacuation system adjusting the outlet port on the filter allows a user to adjust the amount of gases flowing into and out of the smoke evacuation system as required. For example the user could close the outlet port which would effectively turn the smoke evacuation system "off" by restricting flow out of said filter, alternatively the user could open the port to allow gases to flow through the smoke evacuation system, hence turning the smoke evacuation system "on".

The surgical smoke travels through the smoke evacuation system 300 due to the negative pressure gradient that exists. The outlet end of the smoke evacuation system is at a lesser pressure as compared to the pressure at the operational site. The operational site is pressurised due to the pressurised insufflation gases delivered into the operational site. The outlet end of the conduit and filter are at atmospheric pressure which is significantly less than the pressure of the pressurised gases. This negative pressure gradient forces the surgical smoke to flow through the discharge limb 301 of the smoke evacuation system, through the filter 303 and out of the outlet end.

Smoke Evacuation System Discharge Limb

Figure 1:
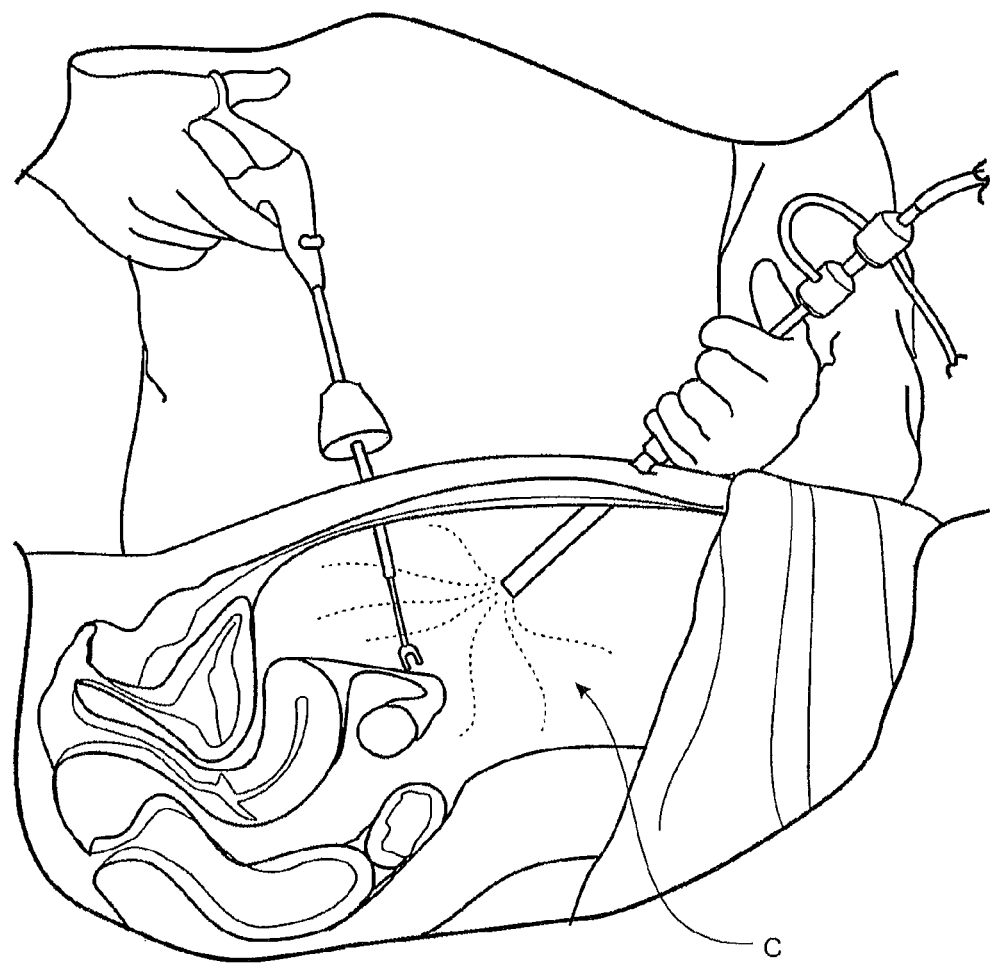
FIG. 1 shows a diagram of a typical laparoscopic procedure, with part of the outer layers of the body not shown so as to show interior detail.

The gases supplied by the insufflation system 100 maybe humidified at the point of entry to the body cavity (i.e. as indicated by item C in FIG. 1). Alternatively the insufflation gases may be provided without any humidification. As the body cavity is already moist and humid, the gases do not tend to lose moisture in the body, and can become fully saturated if they are not already at saturation point. If the gases are dry on entry to the body cavity, they tend to become humidified as they pass through the body cavity, picking up moisture from the damp atmosphere in the body cavity above the internal organs.

When these saturated gases pass out of the abdominal cavity, they pass along the cooler walls of the discharge limb, which is normally around one meter in length or thereabouts. The moisture in the gases tends to condense out of the gas onto the walls of the discharge limb or conduit. The water vapour can also condense on the filter 303. The vapour condensing on the filter 303 and run-off along the discharge limb from moisture which has condensed on the walls can saturate the filter 303 and cause it to become blocked. This potentially causes an increase in back pressure and hinders the ability of the system to clear smoke.

The condensed moisture within the filter 303 can cause the filter medium to become blocked, leading to an increase in back pressure and reduced filter 303 efficiency due to the blockage. This is disadvantageous because the increased back pressure hinders the ability of the system to effectively clear the surgical smoke. The condensation within the filter 303 also may at least partly block the filter media and decrease the efficiency of the filter. The surgical smoke remaining at the operational site within the surgical cavity or within the discharge limb 301 of the evacuation system can be hazardous to the patient since the surgical smoke contains several potential toxins that may become entrained in the surgical cavity or tissue of the patient. The vision of the surgeons can be obstructed or hindered clue to the surgical smoke remaining at the operational site and not being evacuated, potentially leading to a hazardous working environment for the surgeons. The condensation may partially block the filter media resulting in reduced filtration of toxins from the surgical smoke. This could result in potentially harmful substances like odours, surgical smoke, dead cellular matter and so on escaping into the operating theatre.

These sorts of materials can be hazardous to the health and may lead to many health problems for medical practitioners and the patient.

The applicants have carried out testing which indicates that the use of a discharge limb 301 having a breathable wall or the wall of the limb 301 which includes breathable material may help to alleviate this problem. A certain amount of moisture from the expelled gases passes through the wall of the conduit before reaching the filter 303, and therefore there is less moisture in the gas to condense out of the gas and clog the filter 303.

In this context, 'breathable material' means a material that allows the passage of water vapour through the limb to ambient air while substantially preventing the passage of liquid water, water droplets or condensate, or any other components of the surgical smoke (particles, etc) to ambient air. Ambient air in this context refers to the air outside the smoke evacuation limb or discharge limb, and not necessarily only to atmospheric air. In the preferred form the water vapour moves from within the conduit to atmospheric air. In an alternate form instead of the conduit discharging air to atmosphere, the discharge limb may be arranged co-axially with another conduit placed around the outside of the discharge limb. The outer conduit acts like an air jacket and the water vapour from the discharge limb may move from within the discharge limb out to the outer conduit. The outer conduit or air jacket can act to evacuate any water vapour transmitted from the discharge limb to the air in the outer conduit.

The purpose of the breathable discharge limb, or a discharge limb with a breathable region or regions, is to allow passage of water vapour through the wall of the discharge limb to ambient air, away from the expired gases and surgical smoke which in use pass through the discharge limb. The breathable material allows the passage of water vapour through the wall of the discharge limb to ambient air without allowing the passage of liquid water, gases or surgical smoke to ambient air. Materials may be breathable due to their composition, physical structure or a combination thereof. The mechanisms of water vapour transmission through these breathable materials are numerous and known in the art. The purpose of the breathable region or regions of the supply conduit wall is to allow passage of water vapour froth the gases path along independent of specific drain locations. This reduces the build up of condensation within the breathing tube by drying the humidified breathing gases (by transmitting water vapour to the surrounding ambient air) during their flow through the discharge limb. One example material that could be used for the breathable regions of the discharge limb 301 is an activated perfluorinated polymer material. An example of this polymer material is marketed under the trade name NAFION™ by DuPont Fluoro products of Fayetteville USA.

Alternatively, the breathable regions of the conduit may be constructed out of hydrophilic thermoplastics, woven treated fabric products exhibiting breathable characteristics or a hydrophilic polyester block copolymer formed into a homogenous flat film. An example of such a film is sold user the brand SYMPATEX™. A further alternative for the breathable material is ARNITEL™ or GORETEX™. This has been experimentally shown to help to reduce condensation build up within the discharge limb. As a certain amount of the water vapour from the gases passing along the discharge limb diffuses to atmosphere, there is less water vapour in the conduit itself, so there is less likelihood of the filter becoming blocked with condensate, for example.

Ideally, the discharge limb 301 would be formed in such a manner, and will have dimensions so that the wall will allow passage of substantially all, or at least a significant portion, of the moisture in the gases before the gases reach the filter 303. In a practical sense complete drying of the gas is not achievable. The flow rate of the gases is too high, and the amount of moisture in the gases too high, to allow more than a proportion to be passed through the wall. The objective is therefore to produce a discharge limb that will allow enough moisture to pass through the all as possible, so that the filter will not clog during use and before it is replaced. The amount of moisture in the expelled gases passing along the discharge limb will depend on a number of factors, such as the humidity in the gases provided to a user, the humidity generated by the individual user, the length of the surgery, the type of surgery, whether the discharge limb is connected to an external source of vacuum, etc. All these factors mean that the amount of moisture in the gas is highly variable. The applicants propose forming the discharge limb in such a way as to allow enough moisture to pass through the wall to keep the filter unclogged and working effectively for most commonly encountered surgical situations, and to keep the filter as unclogged as possible until it is replaced during normal maintenance of the insufflation circuit.

One factor allowing the passage of moisture through the wall of the discharge limb is the surface area of the wall. The diameter of the discharge limb 301 and the length of the discharge limb 301, also affect the rate of transfer of vapour through the wall, as these have a direct impact on the flow rate of gases within the discharge limb. The applicants have carried out testing using a single type of conduit as the discharge limb and the test results positively indicate that a useful proportion of the water in the discharge limb will pass through the wall before reaching the filter, and that there is therefore value in having a breathable discharge limb. These test results are discussed later as Example 1.

Based on these test results, it is anticipated that smoke evacuation systems having discharge limbs with properties as outlined below will be beneficial and provide surgical teams with a useful choice. Preferably as much of the wall of the discharge limb 301 as possible is made of a breathable material, in order to increase the surface area available for the transfer of water vapour from inside the discharge limb to the outside.

Preferably the length of the discharge limb 301 is at least 400-1500 mm. The discharge limb may be come in two forms. In one form the limb is long enough to contact the floor as it extends from the operating table. In another forth the limb is not long enough to contact the floor. The limb is shorter than the height of the operating table upon which a surgical procedure is taking place.

Preferably the internal diameter of the discharge limb 301 is between 10 mm and 25 mm.

Preferably the surface area of the discharge limb is between 12560 $mm^2$ and 47100 $mm^2$ or any other suitable value.

Preferably at least 10% of the surface area of the wall of the limb comprises a breathable material.

The discharge limb is also preferably substantially flexible. "Flexible" in terms of this context refers to the discharge limb being unable to support its own weight. Flexible also means it is easily bendable without damage or permanent.

All of the materials referred to above can be formed into thin films. A number of ways are described in the art for forming thin flat films or ribbons into discharge limbs. These include helical winding. Alternatively, these materials can be directly extruded to form a discharge limb. Alternatively, it is anticipated that the conduit could be formed from short, ring-shaped portions of material laid and connected in series or end to end. All or some of these portions could be made from breathable material—for example, the breathable sections could alternate with the non-breathable sections. Any of the forming methods known in the art can be used for forming the conduit of the present invention. The conduit could also use a (non-breathable) reinforcing bead wound helically around the conduit, or a longitudinal reinforcing spine or bead, or similar. Annular reinforcing rings could also be located at intervals along the discharge limb. The conduit could also be formed from two ribbons wound as a double helix, with one of the ribbons being breathable, and the other non-breathable.

Discharge Limb Support

The discharge limb 301 may be any suitable length. In one form the discharge limb 301 may be long enough to contact the floor. In another form the limb May not be long enough to contact the floor. Preferably the limb is between 400 min and 600 mm long, the most preferred length being 470 mm. In use the limb hangs downward as it extends away from the surgical site. The filter is the low point when the limb hangs downward, since the filter 303 is at the end of the limb. This can be problematic since moisture built up within the discharge limb runs downward toward the filter attached to the outlet of the discharge limb. This moisture can cause the filter to get clogged and reduce the effectiveness of the smoke evacuation system. The problems of moisture build up and clogged filters have are discussed above.

The smoke evacuation system 300 preferably comprises a smoke evacuation limb support. Various forms of the support are shown in FIGS. 3, 9 10, 11 and 12. The support 320 supports the smoke evacuation limb such that the filter is directed away from the ground. The support 320 holds the limb 301 in such a way that a U bend is formed in the limb. Preferably a section of the smoke evacuation limb is bent to stop condensation flowing toward the filter 303, for example by placing it in the support 320 so as to direct the filter away from the ground. The U bend acts as a water trap for any condensation or moisture built up in the limb and any condensation formed accumulates within the trough formed by the U bend. The U bend is seen in FIGS. 9, 10, 11 and 12.

FIG. 3 shows the preferred location of the support in relation to the other elements of the smoke evacuation system. The support is preferably located near the exit end of the discharge limb, closer to the filter than the patient. Alternatively the support may be located at any point along the discharge limb. The structure of the support will be discussed in more detail with respect to FIGS. 9 to 12.

Figure 10:
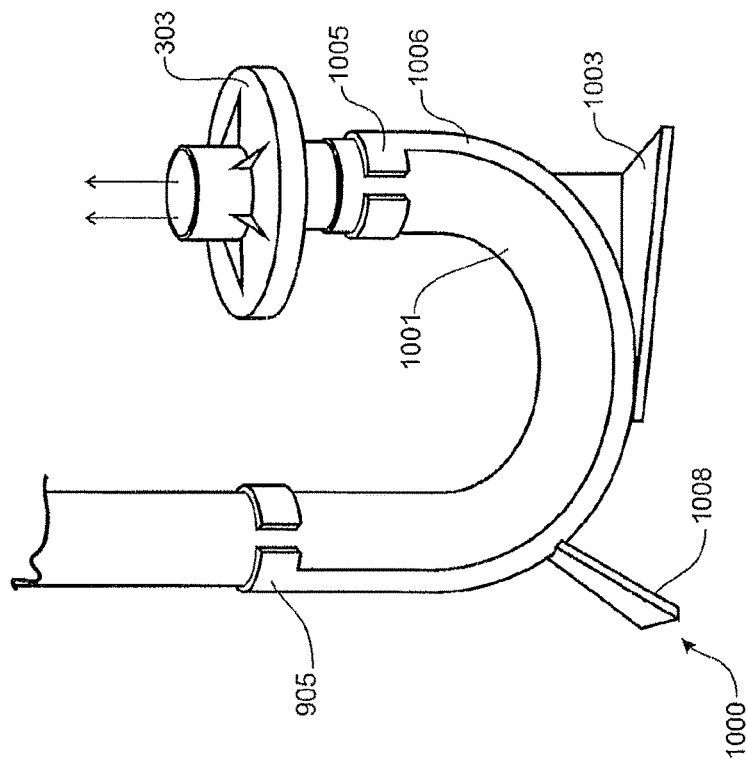
FIG. 10 shows another form of the support having two legs, one leg being substantially larger than the other and providing a stable base for the support.
Figure 9:
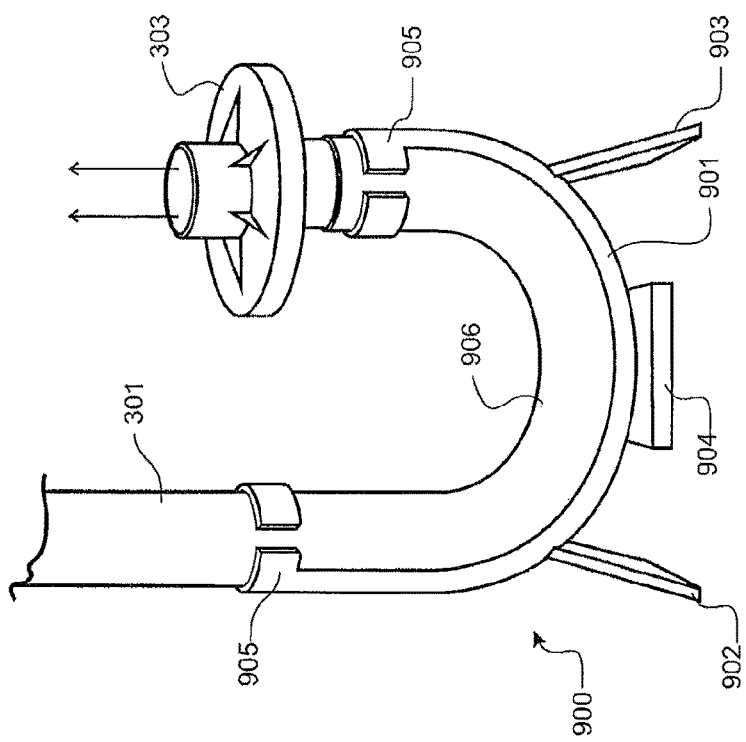
FIG. 9 shows a support to receive and retain the smoke evacuation limb, the support having two legs and a stand member extending from the body of the support.

One forth of the support may include legs attached to extending from the support. The various forms of legged supports are shown in FIGS. 9 and 10. Legged supports can be used when the discharge limb 301 is long enough to contact the ground. The preferred form of legged support is shown in FIG. 9. The support 900 preferably may maintain at least three contact points with the ground to provide maximum stability. The support 900 includes a body 901. The body 901 is preferably substantially curved to form a U shape, as seen in FIG. 9. Alternatively the body may be curved in any other shape that creates a U shaped bend in the discharge limb before the filter 303. The body 901 is preferably made from a substantially rigid material. The support 900 preferably includes at least two receiving features 905. The receiving features 905 receive and retain the discharge limb 301 in the correct orientation. The most preferred orientation is when the filter 303 is directed away from the ground. Most preferably the receiving features are slots or rings, one at each end of the support 901. Alternatively the receiving features may be grooves or clips that can be opened and clipped to receive and retain the limb 301. The limb 301 preferably snap fits into the receiving features 905. The limb 301 can be easily removed from the support 900. The receiving features 905 are preferably formed integral to the body 901. Alternatively the receiving features 905 may be separately formed and connected to the body by any appropriate fastening technique or mechanism. The body 901 of the support 900 preferably has a channel 906 formed within it. The channel 906 is shaped to receive and retain the limb 301 within it. The support 900 may be formed from plastic material. Alternatively the support 900 may be formed from metal or any other suitable rigid material. In the preferred form the support 900 is vacuum formed but may alternatively formed from any other suitable material.

The support may preferably comprise two legs 902, 903 extending from the body of the support. The legs act to prop up the support and allow the support to hold up the limb. The two legs provide two of the contact points with the ground. The body 901 of the support may include a stand member 904 that acts as a third contact point. Preferably the stand member is an elongate member as shown in FIG. 9. Alternatively the stand member 904 may be any other suitable shape that provides a stable contact point with the ground and allows the support to stand. Alternatively the support 900 may not include a stand member 904. The third contact point may be due to the body 901 of the support bearing on the ground and providing stability for the support 900. The support may have multiple legs and multiple ground contact points. Such alternative embodiments are also within the scope of this specification.

A further alternative form of legged support is shown in FIG. 10. The support 1000 may include only two legs 1002, 1003, as shown in FIG. 10. The support 1000 includes a support body 1001. The support body may be substantially similar to the support body 901 described with respect to FIG. 9. The support body 1001 is preferably U shaped as seen in FIG. 10, but could be curved in any other shape. The support 1000 holds the discharge limb such that the filter is not the lowest point of the limb 301. The lowest point of the limb is preferably the lowest point of the U bend. The support body 1001 may include a receiving feature 1005 at each end of the support body 1001. The receiving feature is preferably slot but could be a ring, groove or clip. The receiving feature 1005 receives and retains the discharge limb 301 in the correct orientation. The discharge preferably snap fits into the receiving features 1005. The support body 1001 may also include a channel 1006 to receive and retain the discharge limb 301 within it. The legs 1002, 1003 are specifically designed to keep the support stable when in contact with the ground. The legs may be shaped such that one leg is larger than the Other, the large leg having a large contact area with the ground with a smaller leg providing stability and a second contact point. An example of this is shown in FIG. 10 with leg 1003 being the larger one and leg 1002 being the smaller leg.

In a further alternative form the support may include a righting mass attached to it, or housed within it. The righting mass (not shown) may be a moveable weight like a fluid or ball bearings or any other suitable moving weight. Preferably the righting mass may be housed in one of the legs of the support 900. The righting mass may also be housed in the body 901 of the support 900. Preferably the support is housed substantially in the middle of the support or connected close to the middle of the support for example the righting mass may be housed within or connected near the lowest point of U shaped body 901 of the support. Most preferably the righting mass is housed in the stand member 904 or connected close to the position where the stand member 904 attaches to the support. In an alternative the legs 1002, 1003 of the support 1000 may include a righting mass within one or both of the legs 1002, 1003. In a further alternative one of the legs of the support may be larger than the other and heavier than the other leg or legs. The larger leg may act as a righting mass due to its size or shape or a combination thereof. The leg of the support may take any suitable shape that allows it to act as a righting mass. The righting mass may be formed of any suitable, material like a metal. Preferably the material of the righting mass may be heavier than the support to allow the righting mass to effectively stabilise and correctly orient the support when in use. In a further alternative the support may include multiple righting masses to stabilise the support and ensure the support is oriented the correct way around. The righting mass or masses is advantageous because the righting mass stabilises the support and ensures the support is in the correct orientation in use. The righting mass counteracts any forces or moments that may be applied to the support while in use, for example due to the limb 301 being pulled or the support 900 or 1000 being bumped. The righting mass adds stability to the support to ensure the support remains in the correct orientation. Moving the support from its correct orientation may lead to condensation running toward the filter or may cause damage to the limb 301 or filter 303. The support 900 being in the wrong orientation may also lead to other adverse effects on the smoke evacuation system. The righting mass helps to stabilise the support so that it remains in the correct orientation.

Figures 11, 12:
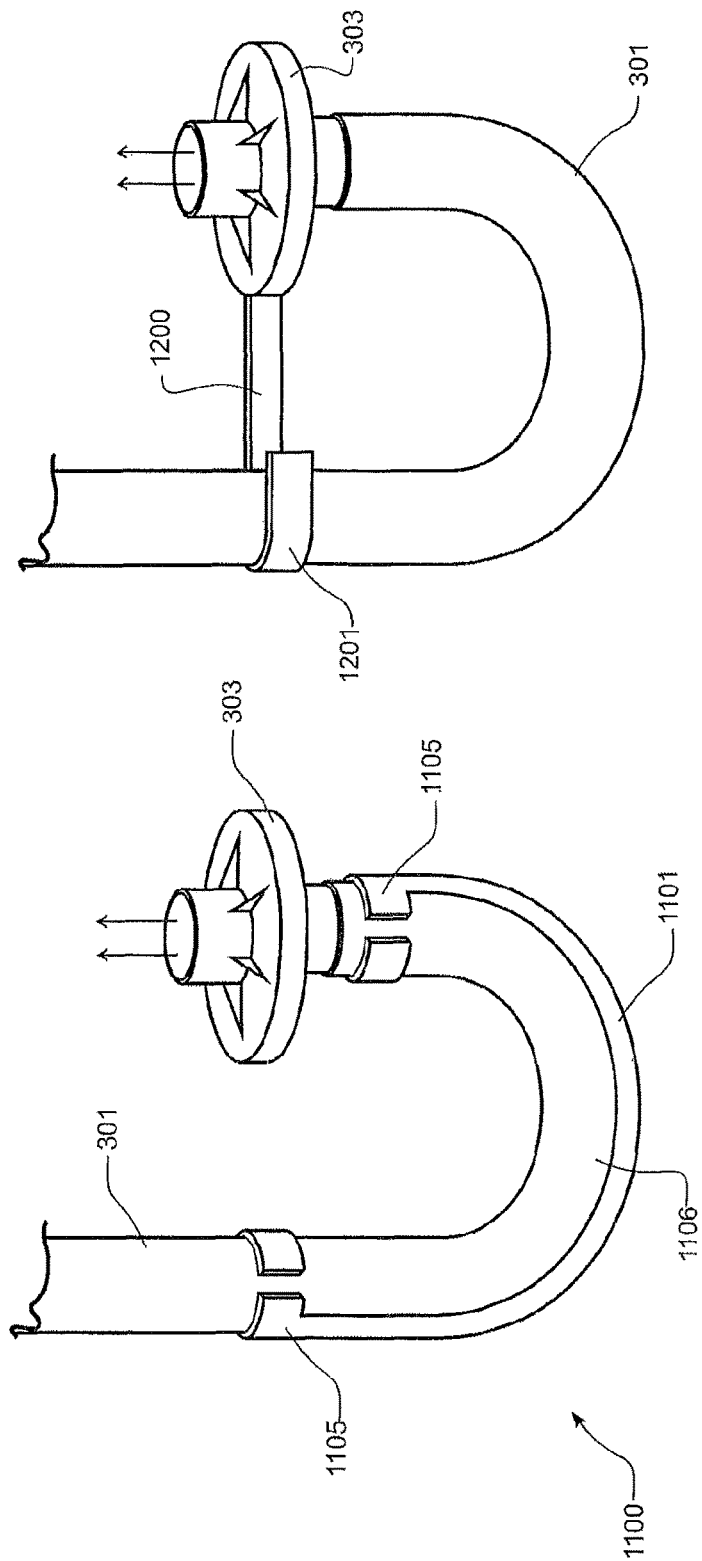
FIG. 11 shows a further form of the support having no legs, just a body to receive and retain the limb.
FIG. 12 shows a further form of the support, the support being a retaining member extending from the filter with a retaining feature at one end of the retaining member to receive and hold the limb.

In an alternative form the support may have no legs, as shown in FIGS. 11 and 12. A legless support may be used when the discharge limb is not long enough to contact the floor. One embodiment of a legless support is shown in FIG. 11. The support 1100 may be attached to another feature like a wall or a bedpost. Attachment may be permanent, for example by a suite or fastening mechanism or attachment may be temporary for example by non permanent adhesive, clips or hook and loop features. In a further alternative form the support may be adhesively attached to another feature. The support 1100, as seen in FIG. 11 preferably includes a support body 1101. The support body 1101 is substantially similar in shape to the support body 901 shown in FIG. 9. The support 1100 is substantially U shaped but alternatively the support 1100 may be in any other curved shape. The support receives and retains the limb 301 and holds the limb 301 in the preferred orientation, where the filter 303 is pointing away from the ground. The support 1100 holds the limb 301 in a way that the filter is not the lowest point of the limb. The support 1100 may also include a receiving feature 1105 at either end or at each end of the support. The receiving feature 1105 is preferably a slot but may be a groove, ring or clip. The receiving feature 1105 receives and retains the discharge limb 301 in the correct orientation. The support body 1101 may also include a channel or groove 1106 in it. The channel 1106 acts to receive and retain the limb 301 within it. The discharge limb 301 preferably fits into the receiving feature 1105 and the channel 1106 by snap fit. Alternatively the limb 301 may be clipped into or retained by the receiving features 1105 in any other suitable way. The support without any legs may also include a righting mass within the support body 1101 or attached to the support body 1101. In one further form the righting mass may be a member protruding from the body of the support. The member may act to counteract any forces or moments applied to the support during use, such that the support remains in the correct orientation.

A further alternative form of a legless support 1200 is shown in FIG. 12. Such a legless support is preferably used with a discharge limb that is not long enough to contact the floor. In one form the support may be a retaining member 1200 that extends from the filter 303 and engages with one part of the discharge limb 301. The retaining member 1200 is preferably an elongate member that extends outward from the filter and engages with part of the limb 301 to bend or contort the limb into a substantially U shape, as shown in FIG. 12. The retaining member 1200 may include a retaining feature 1201 on one end. The retaining feature 1201 may be a hook or a loop. The discharge limb 301 fits into the retaining feature 1201. Alternatively the support 1200 may be a clip that can open and close to receive, and hold the limb 301. Preferably the retaining member 1200 may be formed integral with the filter. Alternatively the retaining member 1200 may have second retaining feature (not shown) on the opposing end of the first retaining feature 1201 that engages with the limb 301, preferably at a point adjacent the filter 303. The retaining member 1200 may be formed from a rigid material like plastic or metal.

As a further alternative, the support may not hold and retain the discharge limb within it. The rigid support may be hollow and tubular shape, such that it forms, a sealed gases pathway and allows smoke to flow through it and out toward the filter. A first end of the support may be connected to the outlet end of the discharge limb and the second end of the support is connected to filter. The gases and/or smoke from the surgical site travel from the discharge limb to the filter through the support. In another forth the second of the filter may be connected to a secondary limb that connects between the support and die filter. The secondary limb may also be similar in structure and material to the discharge limb. The secondary conduit is substantially flexible and preferably at least part of the secondary conduit is formed from a breathable material such that the breathable material allows water vapour to pass out of the secondary conduit to ambient air without allowing the passage of liquid water or surgical smoke and/or gases.

The support connects to the discharge limb, filter and/or the secondary conduit by a threaded connection. Alternatively the support may have couplers on both its ends that connect the support to the discharge limb, filter and/or the secondary conduit. In a further alternative arrangement the support may be connected to the discharge limb, filter and/or the secondary conduit by plastic or solvent welding.

Water Out Alarm

In an insufflation system incorporating a humidification chamber, a minimum level of water should be maintained in the humidification chamber in order for the humidification chamber to have the ability to humidify incoming gases. The insufflation system 100 may be used with the smoke evacuation system 300. When combine the smoke evacuation system includes a humidification chamber 103 and a heater base 102 attached to it and a gases source supplying gases to the humidification chamber and then into the surgical site. The humidification chamber 103 requires a minimum level of water to allow the humidification chamber to adequately humidify incoming gases. Accordingly a health professional or person using the insufflation system needs to keep checking the water level in the humidification chamber and add more water when required. This job can be tedious one and is often overlooked.

One way to measure the amount of water and determine a low water or no water condition in the humidification chamber 103 is to use a flow probe which automatically determines when the water level drops to an insufficient level and raises an alarm.

The preferred method of measuring and monitoring the amount of water in the humidification chamber will be described. A low water, no water or water out condition as referred to in this specification means when there is either no water or d very low water level in the humidification chamber. A very low water level corresponds to a water level that is insufficient for humidification of the insufflation gases. The method to determine a water out condition in a humidification chamber 103 involves measuring the chamber 103 exit temperature, power supplied to the heater base 102 and a change in the gases flow through or into the chamber 103. Water out condition refers to a zero water level or very low water level in the chamber 103. The chamber 103 humidifies insufflation gases passing through it by water vapour created in the chamber 103. The chamber 103 includes a volume of water that is heated by the heater plate 102. At least some of the water in the chamber 103 becomes water vapour when heated by the heater 102. The insufflation gases flowing through the chamber collect the water vapour and are humidified. The water in the chamber 103 reduces due to continuous use and drops to a point where there is not enough water to humidify the insufflation gases. The method described below is the method implemented by the controller to detect a low water level but more preferably a zero water level condition in the chamber 103.

The method involves measuring the exit temperature of the chamber 103, more specifically measuring the temperature of the gases exiting the chamber 103. As the water in the chamber reduces to a level where the gases are not adequately humidified the temperature of the outlet gases reduces. This is because the water vapour imparted into the gases by humidifying is may be at a higher temperature than the gases. The temperature of the gases exiting the chamber 103 reduces when there ds very little or no water in the chamber 103 because there is no energy transferred to the gases by the water vapour. The temperature of gases exiting the chamber 103 is set by the controller 104. The exit temperature is programmed into the controller 104 based on the type of operation and amount of humidity required for the insufflation gases. The controller 104 attempts to counter the decrease in the exit temperature by increasing the heater duty cycle to increase the heating provided by the heater base 102. In the preferred method the controller measures a decreasing temperature of gases exiting the chamber 103 while also monitoring the response of the heater base. If the temperature of the gases exiting the chamber continuously drops as the power supplied to the heater base is constant or increasing indicates a low water or no water situation in the chamber. The controller 104 alerts the user, sounds an alarm or switches off the power to the heater plate when a low or no water situation is detected. The controller preferably switches off the power to the heater base. In addition the controller may also alert the user by sounding a buzzer or displaying a message on a screen 106 attached to the insufflator 101.

The method also measured the flow rate of gases flowing through the chamber 103 for a more accurate measure of the low or no water situation. The temperature of the gases exiting the chamber 103 can also drop if the flow rate of the gases entering and flowing through the chamber 103 increases. The increased flow rate causes a larger volume of insufflation gas to pass through the chamber 103. The larger volume of gases requires more energy from the water vapour, hence leading to a temperature drop as the gases exit. A larger flow rate of gases requires a larger amount of water vapour for the gases to be humidified to a suitable level. The controller compensates for the increased gases flow by increasing the power to the heater base in order to cause more water in the chamber 103 to evaporate such that the gases are humidified to a suitable level. In order to determine a low water or no water condition in the chamber the controller 104 also monitors the gases flow rate through the chamber 103. A low water or no water condition in the chamber 103 is determined when the gases flowing through chamber are not increasing.

The controller 104 measures the outlet temperature of the chamber, meaning the temperature of the gases flowing out of the chamber 103. The controller also measures the power supplied to the heater base 102 and measures the flow rate of gases through the chamber 103. A low water or no water condition is determined if there is a drop in the temperature of gases exiting the chamber 103, while the power to the heater base is constant or increasing and the flow rate of gases through the chamber 103 is substantially constant or not increasing. If the temperature of the gases exiting the chamber 103 begins to drop the controller 104 increases the power to the heater base 102. The controller 104 can determine a low water or no water condition if the temperature of the gases exiting the chamber 103 and the power to the heater base 102 diverge away from each other. This means if the temperature of the gases exiting chamber 103 is continuously decreasing while the power supplied to the heater base 102 continuously increases. A low water or no water is confirmed if for at least two minutes the controller determines the temperature of the gases exiting the chamber 103 is decreasing, the power supplied to the heater is constant and rising and the flow rate of gases through the chamber 103 is constant or not increasing.

The temperature of the gases exiting the chamber can be measured using any suitable temperature sensor. The flow rate of the gases entering the chamber 103 can also be measured by any suitable flow sensor. The preferred sensor for measuring flow rate of gases is hot wire flow sensor like a hot wire anemometer. The temperature sensor may also be a wire based temperature sensor. In the preferred form the temperature sensor and flow sensor are in the same sensor housing. Hot wire flow sensors may register a reduction in flow due to the reduced cooling effect of the lower humidity gases. This generally occurs when there is a low or no water condition in the chamber. The gases flowing through the chamber are inadequately humidified or not humidified at all. The lower humidity gases cause a cooling effect on the wire probe of the hot wire sensor thus causing the sensor to output an increased flow rate reading. The controller also checks for a reduction in flow rate due to this cooling effect. A reduction in flow rate, a reduction in the temperature of the gases exiting the chamber 103 and an increased or constant power to the heater plate all corresponds to a low or no water condition in the chamber. In an attempt to reduce false alarms, the Water out test only functions in a low flow case. When the controller senses a low flow situation it runs the outlined method to measure the water level in the humidification chamber. The low flow empirically acts as a good filter for false alarms. Preferably this method is stored in ROM and implemented by the software based controller. Alternatively the method of measuring the water level may be implemented as an analogue electronic circuit. As a further alternative the method may be implemented as a digital circuit using flip flops, latches etc.

While the invention or inventions are susceptible to embodiment in different forms, specific embodiments are shown in the drawings, and described in detail above. The present disclosure is to be considered an exemplification of the principles of the invention, and is not intended to limit the invention to that as illustrated and described herein.

EXAMPLE 1

Purpose:

The purpose of this testing was to compare, the build up of condensation when using a breathable tube versus a PVC tube when combined with a laparoscopic smoke evacuation filter in conjunction with the Fisher & Paykel Healthcare MR860 Humidification system.

A test was carried out to compare the difference between using a non-breathable PVC tube as the discharge limb in a smoke evacuation system 300 and using a conduit which is at least partly breathable. The test set out to measure which type of conduit or tubing resulted in the least amount condensation forming within the discharge conduit and filter attached to the discharge conduit. The test used an experimental rig to simulate the conditions which would normally be encountered in an insufflated abdominal cavity undergoing surgery.

Figure 4:
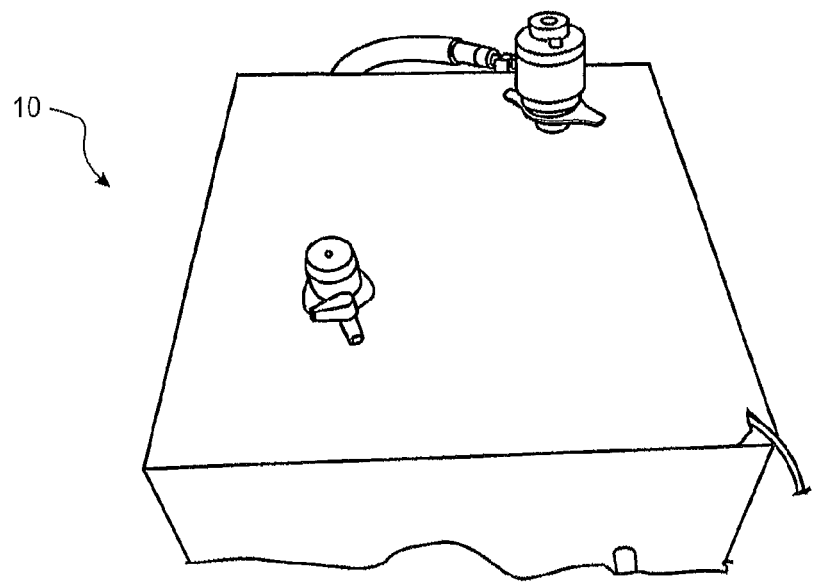
FIG. 4 shows the patient model used to test the effectiveness of a breathable discharge limb used with the smoke evacuation system.

The method steps as performed by the inventors to perform the test are described below:

Method:

Step 1: Set up the patient model with two holes in the lid 20 cm apart, as shown in FIG. 4 by reference 10. Seal the top of each hole with a piece of thin silicone. The silicone will have a hole 50% of the cannula diameter. Add 1 L of water to the model and seal the patient model lid to the container with a silicone sealant. Insulate the patient model fully with polystyrene or similar insulator. Use cloth on the lid and edges to cover the entire patient model.

Step 2: Set the patient model air temperature to 37° C. Have the 11 mm cannula port open and the 5.5 mm cannula port closed. Set up the MR860 heater base and RT350 System as detailed in their user instructions. Connect the luer end of the heated limb to the 11 mm cannula port.

Step 3: Set the insufflator pressure to 12 mm/Hg and the flow rate to 3 L/min. Turn the carbon dioxide bottle on and make sure the insufflator indicates gas is remaining in the bottle. Start die gas flow and switch on the heater base.

Figure 5:
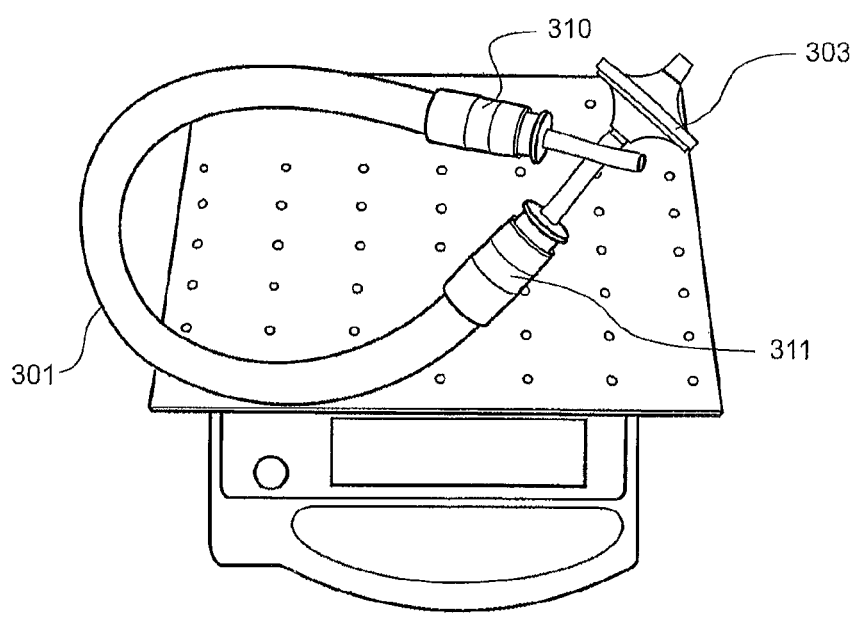
FIG. 5 shows a weighing scale and setup to measure the weight of the smoke evacuation system.

Step 4: Measure and record the dry weight of the smoke evacuation system complete. In the event the scales are too small to accommodate the entire tubing set use a stiff board and then zero the scales prior to placing the tubing set on top as shown in FIG. 5.

Step 5: Connect the smoke evacuation system luer to the 5.5 mm cannula port. Set up the tubing as shown in FIG. 4 so that the tubing angles down slightly after the luer so that any condensation will pool at the bottom. The filter should be a significant height above the exit cannula port as shown in FIG. 6.

Step 6: The setup should look like FIG. 7. Note that in this figure the insufflator, MR860 and MR730 have not been turned on as they, should be. This figure is to only give an overall impression of the layout of the experiment.

Step 7: Once the heater base and patient model have stabilised at their correct temperatures, open the 5.5 mm cannula gas port fully to allow gas to travel out the cannula and through the smoke evacuation system. Reset the gas volume on the insufflator. Let the experiment run for 60 minutes, then turn the 5.5 mm cannula gas port off to stop the flow through the smoke evacuation system. Stop the insufflator gas flow.

Step 8: Carefully disconnect the smoke evacuation system from the cannula ensuring no condensation is split out either end (i.e: hold in a 'U' bend shape). Measure and record the wet weight of the smoke evacuation system complete, similar to step 4. In the event the scales are too small to accommodate the entire tubing set use a stiff board and then zero the scales prior to placing the tubing set on top.

Figure 8A:
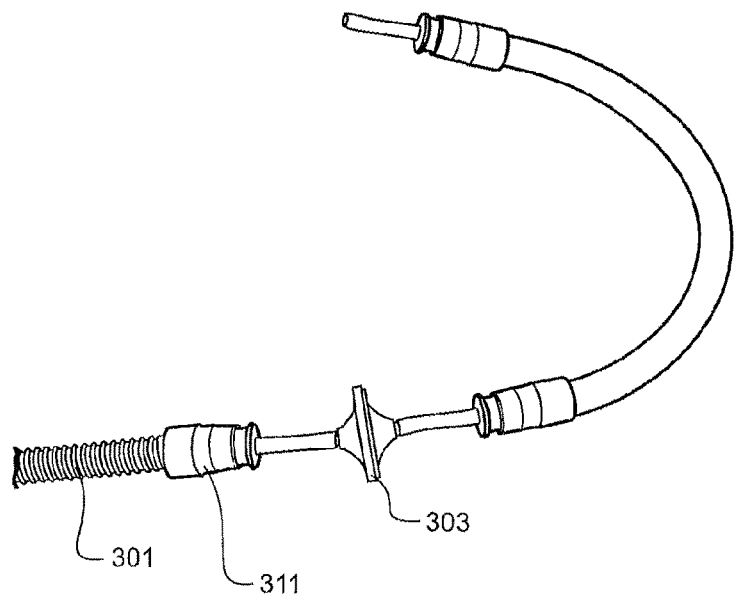
FIG. 8a shows an outlet tube attached to the filter of the smoke evacuation system, the outlet tube being made of a breathable material.
Figure 8B:
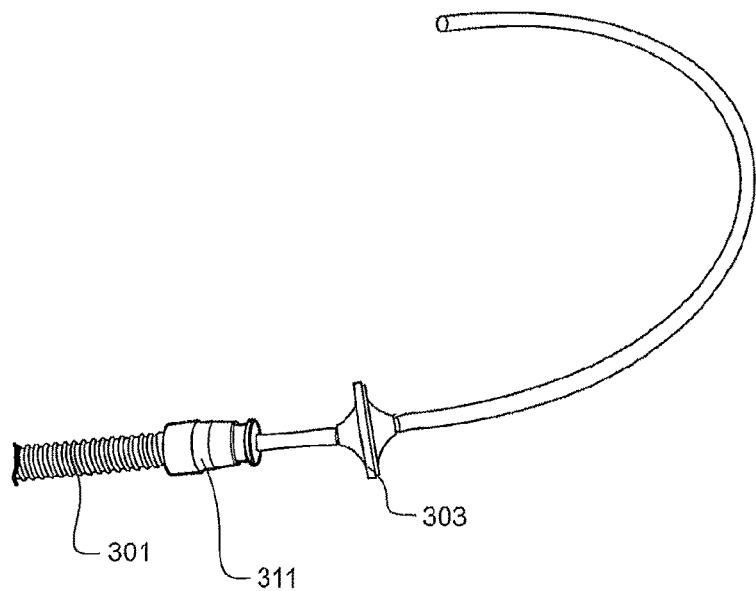
FIG. 8b shows an outlet tube attached to the filter of the smoke evacuation system, the outlet tube being made from a non breathable material.

Step 9: Once the weight has been recorded remove the blue filter tip and connect an air line to the top of the filter as shown in FIGS. 8a and 8b. Flush with dry air for 10 minutes at a low flow rate to dry the filter and tube. Reconnect the blue filter tip and weight the tubing set as in step 4 in preparation for the next test.

Step 10: Change the flow rate to 6 L/min. Check that there is enough water in the RT350 chamber and top up if necessary. Start the gas flow again and wait for the heater base and patient model to stabilise at their correct temperatures. Repeat steps 5 to 9.

Step 11: There are 8 tests in total. The Breathable tubing with combined Clearflow smoke filter is tested twice at 6 L/min and twice at 3 L/min. The same is repeated for the standard PVC Clearflow Smoke Evacuation System.

Results:

A summary of the results is shown below in table 1.

TABLE 1

Results table

| Tube | Flow rate L/min | Dry grams | Wet grams | Difference grams | Average grams |
|---|---|---|---|---|---|
| Breathable tube | 6 | 72.097 | 72.885 | 0.788 | 0.816 |
| Breathable tube | 6 | 72.128 | 72.971 | 0.843 | |
| PVC | 6 | 35.351 | 36.502 | 1.151 | 1.232 |
| PVC | 6 | 35.317 | 36.63 | 1.313 | |
| Breathable tube | 3 | 72.109 | 72.775 | 0.666 | 0.693 |
| Breathable tube | 3 | 72.112 | 72.832 | 0.72 | |
| PVC | 3 | 35.362 | 36.235 | 0.873 | 0.863 |
| PVC | 3 | 35.335 | 36.187 | 0.852 | |

The results show that using the Breathable tube tubing reduced the amount of condensation build up by 33.7% when compared with the PVC tubing when the insufflator is set to 6 L/min. Similarly the results show that the Breathable tubing reduces the amount of condensation build up by 19.6% when compared to with the PVC tubing when the insufflator is set to 3 L/min.

When testing the smoke evacuation filter system with the PVC tube there was significant condensation build up on the walls of the tube right up to the filter despite being higher than the exit port cannula. This was not the case with the Breathable tube. The Breathable tube was connected to both the luer and the filter via a small piece of PVC tube, see FIG. 6. During testing there was significant condensation on the walls of the PVC tube connecting the luer to the breathable tube but no condensation on the tube connecting the breathable tube to the filter.

The results from this experiment clearly show that the smoke evacuation system with a breathable conduit was more effective than the standard smoke evacuation system. This is because there is reduced condensation formed on the tube or filter of the smoke evacuation system with a breathable conduit.

The invention claimed is:

1. A surgical humidification apparatus comprising:
a heater base configured to contact a humidification chamber in use, the humidification chamber adapted to hold a volume of water and having an inlet and an outlet, the inlet in fluid communication with a gases source to receive gases from the gases source in use, the heater base configured to heat the water in the humidification chamber to create vapor to humidify gases passing through the humidification chamber from the inlet to the outlet in use; and
a controller configured to determine a low water or a no water condition of the humidification chamber based at least in part on an increase in power supplied to the heater base.

2. The surgical humidification apparatus of claim 1, further comprising a conduit configured to be coupled to the outlet of the humidification chamber and configured to deliver gases from the outlet to a body cavity for insufflation.

3. The surgical humidification apparatus of claim 1, wherein the controller is configured to determine the low water or the no water condition based at least in part on a continuous drop in a temperature of gases exiting the humidification chamber.

4. The surgical humidification apparatus of claim 1, wherein the controller is configured to determine the low water or the no water condition based at least in part on a constant or decreasing flow rate of gases passing through the humidification chamber.

5. The surgical humidification apparatus of claim 1, wherein the controller is configured to determine the low water or the no water condition based at least in part on a continuous drop in a temperature of gases exiting the humidification chamber and the increase in power supplied to the heater base.

6. The surgical humidification apparatus of claim 1, wherein the controller is configured to determine the low water or the no water condition based at least in part on a continuous drop in a temperature of gases exiting the humidification chamber, the increase in power supplied to the heater base, and a constant or decreasing flow rate of gases passing through the humidification chamber.

7. The surgical humidification apparatus of claim 1, wherein the controller is configured to regulate humidity supplied to the gases passing through the humidification chamber by controlling power supplied to the heater base.

8. The surgical humidification apparatus of claim 1, wherein the controller is configured to switch off power to the heater base if the controller determines the low water or the no water condition exists.

9. The surgical humidification apparatus of claim 1, wherein the controller is configured to sound a buzzer if the controller determines the low water or the no water condition exists.

10. The surgical humidification apparatus of claim 1, wherein the controller is configured to display a message on a screen if the controller determines the low water or the no water condition exists.

11. An insufflation system comprising:
the surgical humidification apparatus of claim 1;
an insufflator in fluid communication with the surgical humidification apparatus; and
a smoke evacuation system.

12. The insufflation system of claim 11, wherein the smoke evacuation system is configured to allow gases to flow from a body cavity to atmosphere, wherein the smoke evacuation system is passive, and wherein a pressure of the smoke evacuation system is greater at an end nearer the body cavity than at an outlet end having an aperture open to atmosphere.

13. The insufflation system of claim 11, the smoke evacuation system comprising a discharge assembly, a discharge limb, and a filter.

14. The insufflation system of claim 13, wherein the discharge limb is flexible and self-supporting.

15. The insufflation system of claim 13, the smoke evacuation system further comprising a support for the discharge limb.

16. The insufflation system of claim 15, the support comprising at least one righting mass configured to stabilize the support, the support configured to create a U shaped bend in the discharge limb, the U shaped bend configured to act as a water trap, the support configured to retain the discharge limb in the U shaped bend such that the filter is not the lowest point of the discharge limb.

17. The insufflation system of claim 13, the smoke evacuation system further comprising a valve positioned between the discharge assembly and the discharge limb.

18. The insufflation system of claim 13, the smoke evacuation system further comprising an adjustable outlet port on the filter.

19. The insufflation system of claim 13, the discharge limb comprising a wall at least partially constructed from a breathable material.

20. The insufflation system of claim 19, wherein the breathable material forms a flow path for vapor from inside the discharge limb to outside the discharge limb.

21. The insufflation system of claim 19, wherein greater than 10% of the wall of the discharge limb is constructed from the breathable material.

22. A surgical humidification apparatus comprising:
a heater base configured to contact a humidification chamber in use, the humidification chamber adapted to hold a volume of water and having an inlet and an outlet, the inlet in fluid communication with a gases source to receive gases from the gases source in use, the heater base configured to heat the water in the humidification chamber to create vapor to humidify gases passing through the humidification chamber from the inlet to the outlet in use; and
a controller configured to determine a low water or a no water condition of the humidification chamber based at least in part on a continuous drop in a temperature of gases exiting the humidification chamber.

23. The surgical humidification apparatus of claim 22, wherein the controller is configured to determine the low water or the no water condition based at least in part on a constant or increasing amount of power supplied to the heater base.

24. The surgical humidification apparatus of claim 22, wherein the controller is configured to determine the low water or the no water condition based at least in part on a constant or increasing amount of power supplied to the heater base and a constant or decreasing flow rate of gases passing through the humidification chamber.

25. The surgical humidification apparatus of claim 22, wherein the controller is configured to sound a buzzer and/or display a message on a screen if the controller determines the low water or the no water condition exists.

26. The surgical humidification apparatus of claim 22, wherein the controller is configured to regulate humidity supplied to the gases passing through the humidification chamber by controlling power supplied to the heater base.

* * * * *

UNITED STATES PATENT AND TRADEMARK OFFICE
CERTIFICATE OF CORRECTION

| | | |
|---|---|---|
| PATENT NO. | : 10,426,902 B2 | Page 1 of 3 |
| APPLICATION NO. | : 15/333011 | |
| DATED | : October 1, 2019 | |
| INVENTOR(S) | : Michael Joseph Blackhurst | |

It is certified that error appears in the above-identified patent and that said Letters Patent is hereby corrected as shown below:

In the Specification

In Column 1, Line 11, change "2010" to --2010,--.

In Column 1, Line 50, change "froth" to --from--.

In Column 2, Line 14, change "upstream," to --upstream--.

In Column 3, Line 34, change "comprising" to --comprising:--.

In Column 3, Line 64, change "so," to --so--.

In Column 4, Line 12 (Approx.), change "shaped," to --shaped--.

In Column 4, Line 18 (Approx.), change "other," to --other--.

In Column 4, Line 66, change "Ti" to --U--.

In Column 5, Line 32 (Approx.), change "an," to --an--.

In Column 5, Line 45, change "to," to --to--.

In Column 5, Line 47, change "discharge" to --discharge limb,--.

In Column 5, Line 48, change "muse" to --in use--.

In Column 5, Line 62, change "condensation," to --condensation--.

In Column 5, Line 66, change "Preferably-said" to --Preferably said--.

Signed and Sealed this
Seventh Day of January, 2020

Andrei Iancu
*Director of the United States Patent and Trademark Office*

CERTIFICATE OF CORRECTION (continued)
U.S. Pat. No. 10,426,902 B2

In Column 6, Line 23, change "discharge," to --discharge--.

In Column 6, Line 25, change "scaled" to --sealed--.

In Column 6, Line 45, change "structure" to --structure to--.

In Column 6, Line 52, change "third," to --third--.

In Column 7, Line 8, change "internal-diameter" to --internal diameter--.

In Column 7, Line 11 (Approx.), change "long:" to --long.--.

In Column 7, Line 15 (Approx.), change "as" to --gas--.

In Column 8, Line 56, change "patient" to --patient,--.

In Column 8, Line 64, change "the" to --site--.

In Column 9, Line 38, change "limb." to --limb--.

In Column 10, Line 20, change "Use" to --use--.

In Column 10, Line 63, change "comprising." to --comprising--.

In Column 11, Line 13 (Approx.), change "at" to --or--.

In Column 12, Line 7, change "402" to --102--.

In Column 12, Line 66, change "iii" to --in--.

In Column 13, Line 4, change "lie" to --be--.

In Column 14, Line 60, change "clue" to --due--.

In Column 15, Line 45, change "froth" to --from--.

In Column 16, Line 10, change "all" to --wall--.

In Column 16, Line 49, change "forth" to --form--.

In Column 17, Line 20, change "May" to --may--.

In Column 17, Line 53, change "forth" to --form--.

In Column 18, Line 16, change "from" to --from a--.

CERTIFICATE OF CORRECTION (continued)
U.S. Pat. No. 10,426,902 B2

In Column 18, Line 56, change "Other," to --other,--.

In Column 19, Line 2, change "support" to --support,--.

In Column 19, Line 15, change "suitable," to --suitable--.

In Column 20, Line 20, change "receive," to --receive--.

In Column 20, Line 30 (Approx.), change "tubular" to --tubular in--.

In Column 20, Line 30 (Approx.), change "forms," to --forms--.

In Column 20, Line 37 (Approx.), change "forth" to --form--.

In Column 20, Line 39, change "die" to --the--.

In Column 21, Line 13, change "d" to --a--.

In Column 21, Line 42, change "ds" to --is--.

In Column 22, Line 61, change "out" to --Out--.

In Column 23, Line 14, change "compare," to --compare--.

In Column 23, Line 43, change "System" to --system--.

In Column 23, Line 48, change "die" to --the--.

In Column 23, Line 62, change "they," to --they--.

In Column 24, Line 7, change "(i.e:" to --(i.e.--.